US010928842B2

(12) United States Patent
Pillai et al.

(10) Patent No.: US 10,928,842 B2
(45) Date of Patent: *Feb. 23, 2021

(54) SYSTEMS AND METHODS FOR ENHANCING WELLNESS ASSOCIATED WITH HABITABLE ENVIRONMENTS

(71) Applicant: Delos Living LLC, New York, NY (US)

(72) Inventors: Dana S. Pillai, New York, NY (US); Nathan B. Stodola, New York, NY (US); Renato P. Termale, New York, NY (US); Richard A. Macary, New York, NY (US)

(73) Assignee: Delos Living LLC, New York, NY (US)

( * ) Notice: Subject to any disclaimer, the term of this patent is extended or adjusted under 35 U.S.C. 154(b) by 31 days.

This patent is subject to a terminal disclaimer.

(21) Appl. No.: 16/444,877

(22) Filed: Jun. 18, 2019

(65) Prior Publication Data

US 2019/0310670 A1    Oct. 10, 2019

Related U.S. Application Data

(63) Continuation of application No. 15/421,022, filed on Jan. 31, 2017, now Pat. No. 10,845,829, and a
(Continued)

(51) Int. Cl.
*G05D 27/02* (2006.01)
*G16H 40/20* (2018.01)
(Continued)

(52) U.S. Cl.
CPC ............... *G05D 27/02* (2013.01); *A61L 2/00* (2013.01); *A61L 9/00* (2013.01); *A61L 9/20* (2013.01);
(Continued)

(58) Field of Classification Search
None
See application file for complete search history.

(56) References Cited

U.S. PATENT DOCUMENTS

| 628,351 A | 7/1899 | O'Neill |
| 828,733 A | 8/1906 | Fuller |

(Continued)

FOREIGN PATENT DOCUMENTS

| CA | 2307458 | 11/2001 |
| CA | 2740939 | 3/2010 |

(Continued)

OTHER PUBLICATIONS

Extended European Search Report issued in EP Application No. 20191237.5 dated Sep. 21, 2020.
(Continued)

*Primary Examiner* — Mohammad Ali
*Assistant Examiner* — Sheela Rao
(74) *Attorney, Agent, or Firm* — Fitch, Even, Tabin & Flannery LLP

(57) ABSTRACT

Environmental characteristics of habitable environments (e.g., hotel or motel rooms, spas, resorts, cruise boat cabins, offices, hospitals and/or homes, apartments or residences) are controlled to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active Illumination addresses various issues, symptoms or syndromes, for instance to maintain a circadian rhythm or cycle, adjust for "jet lag" or season affective disorder, etc. Air quality and attributes are controlled. Scent(s) may be dispersed. Hypoallergenic items (e.g., bedding, linens) may be used. Water quality is controlled. Noise is reduced and
(Continued)

sounds (e.g., masking, music, natural) may be provided. Passive and active pathogen controls are employed. Controls are provided for the occupant and/or facility personnel, as is instruction, and surveys, including assessing wellness.

26 Claims, 7 Drawing Sheets

Related U.S. Application Data continuation of application No. 15/409,233, filed on Jan. 18, 2017, now Pat. No. 10,691,148, which is a continuation of application No. 14/012,444, filed on Aug. 28, 2013, now Pat. No. 9,715,242, and a continuation of application No. 14/012,444, filed on Aug. 28, 2013, now Pat. No. 9,715,242.

(60) Provisional application No. 61/694,125, filed on Aug. 28, 2012.

(51) Int. Cl.
| | | |
|---|---|---|
| *F24F 11/30* | (2018.01) | |
| *H04L 12/28* | (2006.01) | |
| *G05B 15/02* | (2006.01) | |
| *A61M 21/00* | (2006.01) | |
| *F24F 3/12* | (2006.01) | |
| *F24F 11/00* | (2018.01) | |
| *H05B 47/10* | (2020.01) | |
| *H05B 47/105* | (2020.01) | |
| *H05B 47/175* | (2020.01) | |
| *G16H 40/67* | (2018.01) | |
| *A61M 21/02* | (2006.01) | |
| *A61L 9/00* | (2006.01) | |
| *A61L 2/00* | (2006.01) | |
| *B60H 3/00* | (2006.01) | |
| *A61L 9/20* | (2006.01) | |
| *G05B 19/048* | (2006.01) | |
| *G06F 3/16* | (2006.01) | |
| *G06F 19/00* | (2018.01) | |
| *F24F 120/10* | (2018.01) | |
| *F24F 120/14* | (2018.01) | |
| *B05B 1/18* | (2006.01) | |
| *E03C 1/046* | (2006.01) | |
| *A61N 5/06* | (2006.01) | |
| *F24F 3/16* | (2021.01) | |

(52) U.S. Cl.
CPC ........ *A61M 21/0094* (2013.01); *A61M 21/02* (2013.01); *B60H 3/0007* (2013.01); *F24F 3/12* (2013.01); *F24F 11/0008* (2013.01); *F24F 11/30* (2018.01); *G05B 15/02* (2013.01); *G05B 19/048* (2013.01); *G06F 3/165* (2013.01); *G06F 19/3418* (2013.01); *G16H 40/20* (2018.01); *G16H 40/67* (2018.01); *H04L 12/2816* (2013.01); *H04L 12/2827* (2013.01); *H04L 12/2829* (2013.01); *H05B 47/10* (2020.01); *H05B 47/105* (2020.01); *H05B 47/175* (2020.01); *A61L 2209/11* (2013.01); *A61M 2021/0011* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2021/0083* (2013.01); *A61M 2205/0205* (2013.01); *A61M 2205/0238* (2013.01); *A61M 2205/13* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/42* (2013.01); *A61M 2205/50* (2013.01); *A61M 2205/505* (2013.01); *A61M 2205/52* (2013.01); *A61M 2205/6018* (2013.01); *A61M 2205/6054* (2013.01); *A61M 2205/6063* (2013.01); *A61M 2205/7509* (2013.01); *A61M 2205/7518* (2013.01); *A61M 2205/7545* (2013.01); *A61M 2230/005* (2013.01); *A61M 2230/04* (2013.01); *A61M 2230/50* (2013.01); *A61M 2230/63* (2013.01); *A61N 5/0618* (2013.01); *B05B 1/18* (2013.01); *E03C 1/046* (2013.01); *F24F 2003/1689* (2013.01); *F24F 2120/10* (2018.01); *F24F 2120/14* (2018.01); *G05B 2219/2642* (2013.01); *Y02A 90/10* (2018.01)

(56) References Cited

U.S. PATENT DOCUMENTS

| | | |
|---|---|---|
| 853,033 A | 5/1907 | Roberts |
| 1,648,277 A | 11/1927 | Korb |
| 2,184,644 A | 12/1939 | Homberger |
| RE27,027 E | 1/1971 | Cristofv |
| 3,621,838 A | 11/1971 | Harding |
| 3,678,337 A | 7/1972 | Grauvogel |
| 4,074,124 A | 2/1978 | Maute |
| 4,273,999 A | 6/1981 | Pierpoint |
| 4,308,911 A | 1/1982 | Mandl |
| 4,638,853 A | 1/1987 | Papak |
| D295,934 S | 5/1988 | Dyrhood |
| 4,803,625 A | 2/1989 | Fu |
| 4,828,609 A | 5/1989 | Anderson |
| 4,858,609 A | 8/1989 | Cole |
| 4,882,166 A | 11/1989 | Graham |
| 4,893,291 A | 1/1990 | Bick |
| 4,911,166 A | 3/1990 | Leighton |
| 4,911,737 A | 3/1990 | Yehl |
| 4,916,642 A | 4/1990 | Kaiser |
| 4,930,505 A | 6/1990 | Hatje |
| 4,938,582 A | 7/1990 | Leslie |
| 4,947,928 A | 8/1990 | Parker |
| 4,953,784 A | 9/1990 | Yasufuku |
| 4,962,687 A | 10/1990 | Belliveau |
| D312,018 S | 11/1990 | Giesy |
| 5,006,985 A | 4/1991 | Ehret |
| 5,010,777 A | 4/1991 | Yehl |
| 5,043,840 A | 8/1991 | Yehl |
| 5,079,682 A | 1/1992 | Roberts |
| 5,082,173 A | 1/1992 | Poehlman |
| 5,086,385 A | 2/1992 | Launey |
| 5,092,669 A | 3/1992 | Anderson |
| 5,103,391 A | 4/1992 | Barrett |
| 5,121,030 A | 6/1992 | Schott |
| 5,176,133 A | 1/1993 | Czeisler |
| 5,193,900 A | 3/1993 | Yano |
| 5,197,941 A | 3/1993 | Whitaker |
| 5,214,736 A | 5/1993 | Uemiya |
| D335,978 S | 6/1993 | Grahn |
| 5,250,799 A | 10/1993 | Werner |
| 5,259,553 A | 11/1993 | Shyu |
| 5,285,356 A | 2/1994 | Skene |
| D345,071 S | 3/1994 | Gould |
| 5,292,345 A | 3/1994 | Gerardo |
| 5,304,212 A | 4/1994 | Czeisler |
| 5,343,121 A | 8/1994 | Terman |
| 5,344,068 A | 9/1994 | Haessig |
| 5,350,977 A | 9/1994 | Hamamoto |
| 5,357,170 A | 10/1994 | Luchaco |
| 5,395,042 A | 3/1995 | Riley |
| 5,433,923 A | 7/1995 | Wolverton |
| 5,462,485 A | 10/1995 | Kinkead |
| D364,762 S | 12/1995 | Compton |
| D365,484 S | 12/1995 | Trattner, Jr. |

(56) References Cited

U.S. PATENT DOCUMENTS

| | | |
|---|---|---|
| 5,473,537 A | 12/1995 | Glazer |
| 5,503,637 A | 4/1996 | Kyricos |
| 5,545,192 A | 8/1996 | Czeisler |
| 5,589,741 A | 12/1996 | Terman |
| 5,692,501 A | 12/1997 | Minturn |
| 5,721,471 A | 2/1998 | Begemann |
| 5,742,516 A | 4/1998 | Olcerst |
| D396,581 S | 8/1998 | Schubert |
| 5,791,982 A | 8/1998 | Curry |
| 5,805,267 A | 9/1998 | Goldman |
| D401,085 S | 11/1998 | Grant |
| 5,861,717 A | 1/1999 | Begemann |
| 5,892,690 A | 4/1999 | Boatman |
| 5,919,217 A | 7/1999 | Hughes |
| 5,937,387 A | 8/1999 | Summerell |
| 5,963,294 A | 10/1999 | Schiffer |
| 6,053,936 A | 4/2000 | Koyama |
| 6,055,480 A | 4/2000 | Nevo |
| D424,356 S | 5/2000 | Hahn |
| 6,118,230 A | 9/2000 | Fleischmann |
| 6,135,970 A | 10/2000 | Kadhiresan |
| 6,166,496 A | 12/2000 | Lys |
| 6,170,318 B1 | 1/2001 | Lewis |
| 6,197,094 B1 | 3/2001 | Thofelt |
| 6,208,905 B1 | 3/2001 | Giddings |
| 6,235,046 B1 | 5/2001 | Gerdt |
| 6,238,337 B1 | 5/2001 | Kambhatla |
| 6,269,339 B1 | 7/2001 | Silver |
| 6,290,140 B1 | 9/2001 | Pesko |
| 6,331,160 B1 | 12/2001 | Bardy |
| 6,340,868 B1 | 1/2002 | Lys |
| 6,344,641 B1 | 2/2002 | Blalock |
| 6,348,867 B1 | 2/2002 | Myllymaeki |
| 6,350,275 B1 | 2/2002 | Vreman |
| 6,369,716 B1 | 4/2002 | Abbas |
| 6,387,844 B1 | 5/2002 | Fujishima |
| 6,441,558 B1 | 8/2002 | Muthu |
| 6,448,550 B1 | 9/2002 | Nishimura |
| 6,459,919 B1 | 10/2002 | Lys |
| 6,498,440 B2 | 12/2002 | Stam |
| 6,503,462 B1 | 1/2003 | Michalakos |
| 6,507,159 B2 | 1/2003 | Muthu |
| 6,507,709 B2 | 1/2003 | Hirai |
| 6,525,658 B2 | 2/2003 | Streetman |
| 6,535,190 B2 | 3/2003 | Evanicky |
| 6,554,439 B1 | 4/2003 | Teicher |
| 6,567,009 B2 | 5/2003 | Ohishi |
| 6,583,720 B1 | 6/2003 | Quigley |
| D477,158 S | 7/2003 | Calcerano |
| 6,589,912 B2 | 7/2003 | Kawai |
| 6,607,484 B2 | 8/2003 | Suzuki |
| 6,610,127 B2 | 8/2003 | Lu |
| 6,623,512 B1 | 9/2003 | Heller |
| 6,661,798 B2 | 12/2003 | Sano |
| 6,683,419 B2 | 1/2004 | Kriparos |
| 6,691,070 B1 | 2/2004 | Williams |
| 6,711,470 B1 | 3/2004 | Hartenstein |
| 6,720,745 B2 | 4/2004 | Lys |
| 6,727,091 B2 | 4/2004 | Darlington |
| 6,738,551 B2 | 5/2004 | Noda |
| 6,755,783 B2 | 6/2004 | Cosentino |
| 6,756,998 B1 | 6/2004 | Bilger |
| 6,772,016 B1 | 8/2004 | Oern |
| 6,774,802 B2 | 8/2004 | Bachinski |
| 6,782,351 B2 | 8/2004 | Reichel |
| 6,806,659 B1 | 10/2004 | Mueller |
| 6,834,208 B2 | 12/2004 | Gonzales |
| 6,862,529 B2 | 3/2005 | Brown |
| 6,865,428 B2 | 3/2005 | Gonzales |
| 6,878,191 B2 | 4/2005 | Escaffre |
| 6,879,451 B1 | 4/2005 | Hewlett |
| 6,888,453 B2 | 5/2005 | Lutz |
| 6,888,779 B2 | 5/2005 | Mollicone |
| 6,912,429 B1 | 6/2005 | Bilger |
| 6,933,486 B2 | 8/2005 | Pitigoi-Aron |
| 6,967,565 B2 | 11/2005 | Lingemann |
| 6,991,029 B2 | 1/2006 | Orfield |
| 6,992,803 B2 | 1/2006 | Chang |
| 7,014,336 B1 | 3/2006 | Ducharme |
| 7,038,399 B2 | 5/2006 | Lys |
| 7,065,280 B2 | 6/2006 | Ogawa |
| 7,067,995 B2 | 6/2006 | Gunter |
| D526,512 S | 8/2006 | Hahn |
| 7,092,101 B2 | 8/2006 | Brady |
| 7,097,111 B2 | 8/2006 | Riley |
| 7,099,723 B2 | 8/2006 | Gonzales |
| 7,113,086 B2 | 9/2006 | Shorrock |
| D530,940 S | 10/2006 | Raile |
| 7,145,295 B1 | 12/2006 | Lee |
| 7,145,614 B2 | 12/2006 | Lee |
| 7,173,384 B2 | 2/2007 | Plotz |
| 7,190,126 B1 | 3/2007 | Paton |
| 7,202,613 B2 | 4/2007 | Morgan |
| 7,213,940 B1 | 5/2007 | Van De Ven |
| 7,215,086 B2 | 5/2007 | Maxik |
| 7,224,282 B2 | 5/2007 | Terauchi |
| 7,256,554 B2 | 8/2007 | Lys |
| 7,260,950 B2 | 8/2007 | Choi |
| 7,274,160 B2 | 9/2007 | Mueller |
| 7,288,902 B1 | 10/2007 | Melanson |
| 7,298,871 B2 | 11/2007 | Lee |
| 7,302,313 B2 | 11/2007 | Sharp |
| 7,308,296 B2 | 12/2007 | Lys |
| 7,319,298 B2 | 1/2008 | Jungwirth |
| 7,324,874 B2 | 1/2008 | Jung |
| 7,327,337 B2 | 2/2008 | Callahan |
| 7,348,949 B2 | 3/2008 | Lee |
| D566,428 S | 4/2008 | Kester |
| 7,354,172 B2 | 4/2008 | Chemel |
| 7,358,679 B2 | 4/2008 | Lys |
| 7,364,583 B2 | 4/2008 | Rose |
| 7,387,405 B2 | 6/2008 | Ducharme |
| 7,415,310 B2 | 8/2008 | Bovee |
| 7,446,303 B2 | 11/2008 | Maniam |
| 7,453,217 B2 | 11/2008 | Lys |
| 7,457,834 B2 | 11/2008 | Jung |
| 7,520,634 B2 | 4/2009 | Ducharme |
| 7,524,279 B2 | 4/2009 | Auphan |
| 7,536,388 B2 | 5/2009 | Jung |
| 7,545,267 B2 | 6/2009 | Stortoni |
| 7,553,039 B2 | 6/2009 | Harris |
| 7,557,521 B2 | 7/2009 | Lys |
| 7,572,028 B2 | 8/2009 | Mueller |
| 7,573,210 B2 | 8/2009 | Ashdown |
| 7,574,320 B2 | 8/2009 | Corwin |
| 7,577,915 B2 | 8/2009 | Hunter |
| 7,647,285 B2 | 1/2010 | Heckerman |
| 7,652,582 B2 | 1/2010 | Littell |
| 7,659,673 B2 | 2/2010 | Lys |
| 7,676,280 B1 | 3/2010 | Bash |
| 7,679,281 B2 | 3/2010 | Kim |
| 7,680,745 B2 | 3/2010 | Hunter |
| 7,689,437 B1 | 3/2010 | Teller |
| 7,759,854 B2 | 7/2010 | Miller |
| 7,767,280 B2 | 8/2010 | Klasen-Memmer |
| 7,772,965 B2 | 8/2010 | Farhan |
| 7,827,039 B2 | 11/2010 | Butcher |
| 7,828,205 B2 | 11/2010 | Cronin |
| 7,839,275 B2 | 11/2010 | Spalink |
| 7,840,310 B2 | 11/2010 | Orfield |
| 7,843,353 B2 | 11/2010 | Pan |
| 7,848,945 B2 | 12/2010 | Rozell |
| D632,102 S | 2/2011 | Sato |
| D634,952 S | 3/2011 | Gile |
| 7,901,071 B1 | 3/2011 | Kulas |
| 7,906,789 B2 | 3/2011 | Jung |
| 7,918,406 B2 | 4/2011 | Rosen |
| 7,918,407 B2 | 4/2011 | Patch |
| 7,953,678 B2 | 5/2011 | Hunter |
| 7,967,731 B2 | 6/2011 | Kil |
| 7,973,759 B2 | 7/2011 | Huang |
| 7,977,904 B2 | 7/2011 | Berman |
| 8,028,706 B2 | 10/2011 | Skene |
| 8,038,615 B2 | 10/2011 | Gobeyn |

(56) References Cited

U.S. PATENT DOCUMENTS

| | | |
|---|---|---|
| 8,064,295 B2 | 11/2011 | Palmer |
| 8,066,405 B2 | 11/2011 | Simon |
| 8,086,407 B2 | 12/2011 | Chan |
| 8,100,552 B2 | 1/2012 | Spero |
| 8,100,746 B2 | 1/2012 | Heidel |
| 8,143,792 B2 | 3/2012 | Joo |
| 8,147,302 B2 | 4/2012 | Desrochers |
| 8,154,398 B2 | 4/2012 | Rolf |
| 8,159,150 B2 | 4/2012 | Ashdown |
| 8,188,873 B2 | 5/2012 | Barth |
| 8,200,744 B2 | 6/2012 | Jung |
| D666,123 S | 8/2012 | Sichello |
| 8,253,349 B2 | 8/2012 | Shteynberg |
| 8,271,575 B2 | 9/2012 | Hunter |
| 8,308,784 B2 | 11/2012 | Streeter |
| 8,321,192 B2 | 11/2012 | Boyce |
| 8,344,665 B2 | 1/2013 | Verfuerth |
| 8,352,408 B2 | 1/2013 | Guillama |
| 8,358,214 B2 | 1/2013 | Amigo |
| 8,359,208 B2 | 1/2013 | Slutzky |
| 8,380,359 B2 | 2/2013 | Duchene |
| 8,392,025 B2 | 3/2013 | Orfield |
| 8,429,223 B2 | 4/2013 | Gilley |
| 8,436,556 B2 | 5/2013 | Eisele |
| 8,446,275 B2 | 5/2013 | Utter, II |
| 8,454,729 B2 | 6/2013 | Mittelmark |
| 8,484,153 B2 | 7/2013 | Mott |
| 8,490,006 B1 | 7/2013 | Reeser |
| 8,497,871 B2 | 7/2013 | Zulch |
| 8,506,612 B2 | 8/2013 | Ashdown |
| 8,508,169 B2 | 8/2013 | Zaharchuk |
| 8,515,785 B2 | 8/2013 | Clark |
| 8,527,213 B2 | 9/2013 | Kailas |
| 8,543,244 B2 | 9/2013 | Keeling |
| 8,558,466 B2 | 10/2013 | Curasi |
| 8,558,687 B2 | 10/2013 | Haupt |
| 8,609,121 B2 | 12/2013 | Averett |
| 8,640,038 B1 | 1/2014 | Reeser |
| 8,660,861 B2 | 2/2014 | Chun |
| 8,666,666 B2 | 3/2014 | Bassa |
| 8,674,842 B2 | 3/2014 | Zishaan |
| 8,690,771 B2 | 4/2014 | Wekell |
| 8,707,619 B2 | 4/2014 | Edwards |
| 8,716,952 B2 | 5/2014 | Van De Ven |
| 8,755,942 B2 | 6/2014 | Bonilla |
| 8,760,370 B2 | 6/2014 | Maxik |
| 8,795,169 B2 | 8/2014 | Cosentino |
| 8,801,636 B2 | 8/2014 | Lewicke |
| 8,836,243 B2 | 9/2014 | Eisele |
| 8,852,254 B2 | 10/2014 | Moscovici |
| 8,855,757 B2 | 10/2014 | Kapoor |
| 8,862,532 B2 | 10/2014 | Beaulieu |
| 8,870,740 B2 | 10/2014 | Clegg |
| 8,896,427 B1 | 11/2014 | Ramirez |
| 8,907,803 B2 | 12/2014 | Martin |
| 8,924,026 B2 | 12/2014 | Federspiel |
| 8,961,414 B2 | 2/2015 | Teller |
| 8,979,913 B2 | 3/2015 | D Ambrosio |
| 8,986,427 B2 | 3/2015 | Hauville |
| 9,007,877 B2 | 4/2015 | Godlieb |
| 9,010,019 B2 | 4/2015 | Mittelmark |
| 9,015,610 B2 | 4/2015 | Hunter |
| 9,020,647 B2 | 4/2015 | Johnson |
| 9,044,567 B2 | 6/2015 | Poirrier |
| 9,066,405 B2 | 6/2015 | Van De Ven |
| D734,958 S | 7/2015 | Gosling |
| 9,095,029 B2 | 7/2015 | Lu |
| D737,078 S | 8/2015 | McKinney |
| 9,098,114 B2 | 8/2015 | Potter |
| 9,104,183 B2 | 8/2015 | Zheng |
| 9,118,499 B2 | 8/2015 | Hunter |
| 9,125,257 B2 | 9/2015 | Eisele |
| 9,125,274 B1 | 9/2015 | Brunault |
| 9,147,296 B2 | 9/2015 | Ricci |
| 9,154,559 B1 | 10/2015 | Bovee |
| 9,155,165 B2 | 10/2015 | Chobot |
| 9,204,518 B2 | 12/2015 | Jung |
| 9,220,202 B2 | 12/2015 | Maxik |
| 9,226,371 B2 | 12/2015 | Mohan |
| 9,230,064 B2 | 1/2016 | Yanev |
| 9,230,560 B2 | 1/2016 | Ehsani |
| 9,236,026 B2 | 1/2016 | Jia |
| 9,248,309 B2 | 2/2016 | Pugh |
| 9,297,748 B2 | 3/2016 | Risk |
| 9,306,763 B2 | 4/2016 | Tatzel |
| 9,326,363 B2 | 4/2016 | Godlieb |
| 9,345,091 B2 | 5/2016 | Pickard |
| 9,360,731 B2 | 6/2016 | Berman |
| 9,370,689 B2 | 6/2016 | Guillama |
| D761,598 S | 7/2016 | Goodman |
| 9,392,665 B2 | 7/2016 | Eisele |
| 9,410,664 B2 | 8/2016 | Krames |
| 9,420,667 B2 | 8/2016 | Mohan |
| 9,429,009 B2 | 8/2016 | Paulk |
| 9,430,617 B2 | 8/2016 | Brust |
| 9,430,927 B2 | 8/2016 | Yu |
| 9,456,482 B1 | 9/2016 | Pope |
| 9,465,392 B2 | 10/2016 | Bradley |
| 9,493,112 B2 | 11/2016 | Thomas |
| 9,501,049 B2 | 11/2016 | Balakrishnan |
| 9,510,426 B2 | 11/2016 | Chemel |
| 9,526,455 B2 | 12/2016 | Horseman |
| 9,576,939 B2 | 2/2017 | Roth |
| 9,593,861 B1 | 3/2017 | Burnett |
| 9,595,118 B2 | 3/2017 | Maxik |
| 9,609,724 B2 | 3/2017 | Bulut |
| 9,615,429 B2 | 4/2017 | Roosli |
| 9,636,520 B2 | 5/2017 | Pedersen |
| 9,642,209 B2 | 5/2017 | Eisele |
| 9,655,195 B2 | 5/2017 | Tseng |
| 9,696,052 B2 | 7/2017 | Malchiondo |
| 9,699,874 B2 | 7/2017 | Phillips |
| 9,715,242 B2 | 7/2017 | Pillai |
| 9,730,298 B2 | 8/2017 | Vangeel |
| 9,788,373 B1 | 10/2017 | Chowdhury |
| 9,827,439 B2 | 11/2017 | Maxik |
| 9,839,083 B2 | 12/2017 | Van De Ven |
| 9,887,854 B2 | 2/2018 | Park |
| 9,890,969 B2 | 2/2018 | Martin |
| 9,907,149 B1 | 2/2018 | Dolan |
| 9,909,772 B2 | 3/2018 | Bazar |
| 9,915,438 B2 | 3/2018 | Cheatham, III |
| 9,924,243 B2 | 3/2018 | Lupien |
| 9,933,182 B2 | 4/2018 | Alfakhrany |
| 9,939,823 B2 | 4/2018 | Ovadia |
| 9,952,614 B2 | 4/2018 | Hunter |
| 9,955,423 B2 | 4/2018 | Kates |
| 9,955,550 B2 | 4/2018 | Baek |
| 9,958,180 B2 | 5/2018 | Mahar |
| 9,959,997 B2 | 5/2018 | Bailey |
| 9,984,590 B2 | 5/2018 | Stevens |
| 9,986,313 B2 | 5/2018 | Schwarzkopf |
| 10,001,789 B2 | 6/2018 | Hunka |
| 10,022,556 B1 | 7/2018 | Holbert |
| 10,024,699 B2 | 7/2018 | Rapetti |
| 10,030,833 B2 | 7/2018 | Adler |
| 10,031,973 B2 | 7/2018 | Dey |
| 10,039,169 B2 | 7/2018 | Chen |
| 10,042,336 B2 | 8/2018 | Cipollo |
| 10,047,971 B2 | 8/2018 | Nyamjav |
| 10,051,707 B2 | 8/2018 | Deixler |
| 10,052,061 B2 | 8/2018 | Raymann |
| 10,054,534 B1 | 8/2018 | Nourbakhsh |
| 10,057,963 B2 | 8/2018 | Mead |
| 10,068,297 B2 | 9/2018 | Hull Roskos |
| 10,072,866 B2 | 9/2018 | Bazar |
| 10,075,757 B2 | 9/2018 | Ugan |
| 10,078,865 B2 | 9/2018 | Joshi |
| 10,088,577 B2 | 10/2018 | Klein |
| 10,091,017 B2 | 10/2018 | Landow |
| 10,091,303 B1 | 10/2018 | Ledvina |
| 10,178,972 B2 | 1/2019 | Raymann |
| 2002/0072322 A1 | 6/2002 | Sharp |
| 2002/0096121 A1 | 7/2002 | Ingman |

(56) References Cited

U.S. PATENT DOCUMENTS

| | | |
|---|---|---|
| 2002/0119281 A1 | 8/2002 | Higgins |
| 2002/0128864 A1 | 9/2002 | Maus |
| 2002/0163529 A1 | 11/2002 | Evanicky |
| 2002/0187082 A1 | 12/2002 | Wu |
| 2003/0100837 A1 | 5/2003 | Lys |
| 2003/0133292 A1 | 7/2003 | Mueller |
| 2003/0199244 A1 | 10/2003 | Siddaramanna |
| 2003/0209140 A1 | 11/2003 | Kutt |
| 2003/0209501 A1 | 11/2003 | Leung |
| 2004/0002792 A1 | 1/2004 | Hoffknecht |
| 2004/0060677 A1 | 4/2004 | Huang |
| 2004/0065098 A1 | 4/2004 | Choi |
| 2004/0105264 A1 | 6/2004 | Spero |
| 2004/0160199 A1 | 8/2004 | Morgan |
| 2004/0176666 A1 | 9/2004 | Chait |
| 2004/0178751 A1 | 9/2004 | Mueller |
| 2004/0212321 A1 | 10/2004 | Lys |
| 2004/0245351 A1 | 12/2004 | Orfield |
| 2004/0264193 A1 | 12/2004 | Okumura |
| 2004/0267385 A1 | 12/2004 | Lingemann |
| 2005/0110416 A1 | 5/2005 | Veskovic |
| 2005/0151489 A1 | 7/2005 | Lys |
| 2005/0177957 A1 | 8/2005 | Long |
| 2005/0191505 A1 | 9/2005 | Akarsu |
| 2005/0200578 A1 | 9/2005 | Lee |
| 2005/0213353 A1 | 9/2005 | Lys |
| 2005/0214533 A1 | 9/2005 | Shimosaki |
| 2005/0218870 A1 | 10/2005 | Lys |
| 2005/0225976 A1 | 10/2005 | Zampini |
| 2005/0231133 A1 | 10/2005 | Lys |
| 2005/0236998 A1 | 10/2005 | Mueller |
| 2005/0253533 A1 | 11/2005 | Lys |
| 2006/0000257 A1* | 1/2006 | Samadpour ............ G16H 50/80 73/23.2 |
| 2006/0002110 A1 | 1/2006 | Dowling |
| 2006/0017928 A1 | 1/2006 | Crowther |
| 2006/0018118 A1 | 1/2006 | Lee |
| 2006/0018428 A1 | 1/2006 | Li |
| 2006/0103728 A1 | 5/2006 | Ishigami |
| 2006/0106437 A1 | 5/2006 | Czeisler |
| 2006/0111944 A1 | 5/2006 | Sirmans, Jr. |
| 2006/0154596 A1 | 7/2006 | Meneely, Jr. |
| 2006/0162552 A1 | 7/2006 | Yost |
| 2006/0172579 A1 | 8/2006 | Murphy |
| 2006/0173580 A1 | 8/2006 | Desrochers |
| 2006/0184283 A1 | 8/2006 | Lee |
| 2006/0207730 A1 | 9/2006 | Berman |
| 2006/0246149 A1 | 11/2006 | Buchholz |
| 2007/0001617 A1 | 1/2007 | Pogodayev |
| 2007/0024210 A1 | 2/2007 | Zwanenburg |
| 2007/0115665 A1 | 5/2007 | Mueller |
| 2007/0162858 A1 | 7/2007 | Hurley |
| 2007/0198226 A1 | 8/2007 | Lee |
| 2007/0240437 A1 | 10/2007 | Yonezawa |
| 2008/0031832 A1 | 2/2008 | Wakefield |
| 2008/0103561 A1 | 5/2008 | Moscovici |
| 2008/0146892 A1 | 6/2008 | Leboeuf |
| 2008/0182506 A1 | 7/2008 | Jackson |
| 2008/0224121 A1 | 9/2008 | Bose |
| 2008/0225021 A1 | 9/2008 | Hekstra |
| 2008/0246629 A1 | 10/2008 | Tsui |
| 2008/0294012 A1 | 11/2008 | Kurtz |
| 2008/0297027 A1 | 12/2008 | Miller |
| 2009/0015403 A1 | 1/2009 | Kuris |
| 2009/0065596 A1 | 3/2009 | Seem |
| 2009/0068089 A1 | 3/2009 | Hussain |
| 2009/0104086 A1 | 4/2009 | Zax |
| 2009/0126382 A1 | 5/2009 | Rubino |
| 2009/0128044 A1 | 5/2009 | Nevins |
| 2009/0169425 A1 | 7/2009 | Park |
| 2009/0177613 A1 | 7/2009 | Martinez |
| 2009/0223126 A1 | 9/2009 | Garner |
| 2009/0241496 A1 | 10/2009 | Pintault |
| 2009/0242485 A1 | 10/2009 | Cabados |
| 2009/0243517 A1 | 10/2009 | Verfuerth |
| 2009/0273470 A1 | 11/2009 | Sinkevicius |
| 2009/0292180 A1 | 11/2009 | Mirow |
| 2010/0021710 A1 | 1/2010 | Hunt |
| 2010/0084996 A1 | 4/2010 | Van De Sluis |
| 2010/0119461 A1 | 5/2010 | Bicard-Benhamou |
| 2010/0146855 A1 | 6/2010 | Ma |
| 2010/0169108 A1 | 7/2010 | Karkanias |
| 2010/0185064 A1 | 7/2010 | Bandic |
| 2010/0197495 A1 | 8/2010 | Filippini |
| 2010/0217099 A1 | 8/2010 | Leboeuf |
| 2010/0265803 A1 | 10/2010 | Lee |
| 2010/0277106 A1 | 11/2010 | Baaijens |
| 2010/0289643 A1 | 11/2010 | Trundle |
| 2010/0298981 A1 | 11/2010 | Chamorro |
| 2011/0010014 A1 | 1/2011 | Oexman |
| 2011/0066465 A1 | 3/2011 | Orfield |
| 2011/0084614 A1 | 4/2011 | Eisele |
| 2011/0190913 A1 | 8/2011 | Van De Sluis |
| 2012/0011033 A1 | 1/2012 | Salgia |
| 2012/0019386 A1 | 1/2012 | Doraiswami |
| 2012/0031984 A1 | 2/2012 | Feldmeier |
| 2012/0064818 A1 | 3/2012 | Kurelowech |
| 2012/0072032 A1 | 3/2012 | Powell |
| 2012/0158203 A1 | 6/2012 | Feldstein |
| 2012/0176041 A1 | 7/2012 | Birru |
| 2012/0206726 A1 | 8/2012 | Pervez |
| 2012/0279120 A1 | 11/2012 | Prescott |
| 2012/0298599 A1 | 11/2012 | Sichello |
| 2013/0027637 A1 | 1/2013 | Hosoki |
| 2013/0035208 A1 | 2/2013 | Dalebout |
| 2013/0065098 A1 | 3/2013 | Ohkawa |
| 2013/0081541 A1 | 4/2013 | Hasenoehrl |
| 2013/0102852 A1 | 4/2013 | Kozloski |
| 2013/0119891 A1 | 5/2013 | Herremans |
| 2013/0134962 A1* | 5/2013 | Kamel .............. H02J 13/00034 324/103 R |
| 2013/0141235 A1 | 6/2013 | Utter, II |
| 2013/0208576 A1 | 8/2013 | Loree, IV |
| 2013/0229114 A1 | 9/2013 | Eisele |
| 2013/0276371 A1 | 10/2013 | Birru |
| 2013/0342111 A1* | 12/2013 | Mohan .................. H05B 47/19 315/152 |
| 2014/0058566 A1 | 2/2014 | Rains, Jr. |
| 2014/0067130 A1 | 3/2014 | Pillai |
| 2014/0093551 A1 | 4/2014 | Averett |
| 2014/0099348 A1 | 4/2014 | Averett |
| 2014/0243935 A1 | 8/2014 | Brainard |
| 2014/0283450 A1 | 9/2014 | Darlington |
| 2014/0298719 A1 | 10/2014 | MacKin |
| 2014/0318011 A1 | 10/2014 | Järvinen |
| 2015/0015152 A1 | 1/2015 | Aboulnaga |
| 2015/0052975 A1 | 2/2015 | Martin |
| 2015/0066578 A1* | 3/2015 | Manocchia ............ G16H 50/30 705/7.28 |
| 2015/0088786 A1 | 3/2015 | Anandhakrishnan |
| 2015/0102730 A1 | 4/2015 | Eisele |
| 2015/0126806 A1* | 5/2015 | Barroso ................ A61M 21/02 600/27 |
| 2015/0212057 A1 | 7/2015 | Darveau |
| 2015/0234369 A1 | 8/2015 | Wen |
| 2015/0309484 A1 | 10/2015 | Lyman |
| 2015/0382427 A1 | 12/2015 | Eisele |
| 2016/0019813 A1 | 1/2016 | Mullen |
| 2016/0203700 A1 | 7/2016 | Bruhn |
| 2016/0206898 A1 | 7/2016 | Brainard |
| 2016/0213946 A1 | 7/2016 | Brainard |
| 2016/0231014 A1 | 8/2016 | Ro |
| 2016/0253802 A1 | 9/2016 | Venetianer |
| 2016/0313245 A1 | 10/2016 | Sato |
| 2016/0339203 A1 | 11/2016 | Krames |
| 2017/0023225 A1 | 1/2017 | Chen |
| 2017/0053068 A1 | 2/2017 | Pillai |
| 2017/0065792 A1 | 3/2017 | Bonvallet |
| 2017/0068782 A1 | 3/2017 | Pillai |
| 2017/0136206 A1 | 5/2017 | Pillai |
| 2017/0139386 A1 | 5/2017 | Pillai |
| 2017/0162548 A1 | 6/2017 | Roth |
| 2017/0189640 A1 | 7/2017 | Sadwick |
| 2017/0191695 A1 | 7/2017 | Bruhn |

(56) References Cited

U.S. PATENT DOCUMENTS

| | | |
|---|---|---|
| 2017/0196510 A1 | 7/2017 | Ouwerkerk |
| 2017/0238401 A1 | 8/2017 | Sadwick |
| 2017/0259079 A1 | 9/2017 | Grajcar |
| 2017/0299210 A1 | 10/2017 | Nyamjav |
| 2017/0319816 A1 | 11/2017 | Sokol |
| 2017/0325310 A1 | 11/2017 | Chen |
| 2017/0326380 A1 | 11/2017 | Moore-Ede |
| 2017/0348506 A1 | 12/2017 | Berman |
| 2017/0356670 A1 | 12/2017 | Zhang |
| 2017/0359879 A1 | 12/2017 | Eisele |
| 2018/0042077 A1 | 2/2018 | Riley |
| 2018/0043130 A1 | 2/2018 | Moore Ede |
| 2018/0077767 A1 | 3/2018 | Soler |
| 2018/0149802 A1 | 5/2018 | Krames |
| 2018/0160944 A1 | 6/2018 | Aubert |
| 2018/0206783 A1 | 7/2018 | Yoon |
| 2018/0207445 A1 | 7/2018 | Maxik |
| 2018/0285934 A1 | 10/2018 | Baughman |
| 2018/0295696 A1 | 10/2018 | Li |
| 2018/0295704 A1 | 10/2018 | Haverlag |
| 2018/0311464 A1 | 11/2018 | Krames |
| 2018/0318602 A1 | 11/2018 | Ciccarelli |
| 2018/0320919 A1 | 11/2018 | Tang |
| 2018/0322240 A1 | 11/2018 | Goyal |
| 2018/0322253 A1 | 11/2018 | Goyal |
| 2018/0331845 A1 | 11/2018 | Warren |
| 2018/0339127 A1 | 11/2018 | Van Reen |
| 2018/0349689 A1 | 12/2018 | Lee |
| 2018/0349945 A1 | 12/2018 | Jayaraman |
| 2018/0351758 A1 | 12/2018 | Becker |
| 2018/0351761 A1 | 12/2018 | Li |
| 2018/0353108 A1 | 12/2018 | Prate |
| 2019/0014643 A1 | 1/2019 | Gharabegian |
| 2019/0028549 A1 | 1/2019 | Ledvina |
| 2019/0046109 A1 | 2/2019 | Lewis |

FOREIGN PATENT DOCUMENTS

| | | |
|---|---|---|
| CN | 1150882 | 5/1997 |
| CN | 1544222 | 11/2004 |
| CN | 101421558 | 4/2009 |
| CN | 201414191 Y | 2/2010 |
| CN | 202551821 | 11/2012 |
| CN | 103040443 A | 4/2013 |
| CN | 103197659 A | 7/2013 |
| CN | 103277870 | 9/2013 |
| CN | 203175090 U | 9/2013 |
| CN | 103531174 A | 1/2014 |
| CN | 103604198 A | 2/2014 |
| CN | 203454309 U | 2/2014 |
| CN | 204759076 | 11/2015 |
| EP | 1067825 | 1/2001 |
| EP | 1821582 | 8/2007 |
| EP | 2132960 | 12/2009 |
| EP | 2431541 | 3/2012 |
| EP | 2488912 | 8/2012 |
| JP | S60110520 A | 6/1985 |
| JP | H0552361 A | 3/1993 |
| JP | H0658593 A | 3/1994 |
| JP | H06159763 A | 6/1994 |
| JP | H06225858 A | 8/1994 |
| JP | H09303842 A | 11/1997 |
| JP | H10238089 A | 9/1998 |
| JP | 2000130828 | 5/2000 |
| JP | 2000294388 | 10/2000 |
| JP | 2001224078 | 8/2001 |
| JP | 2001286226 | 10/2001 |
| JP | 2001314882 | 11/2001 |
| JP | 2002042546 A | 2/2002 |
| JP | 2002059152 A | 2/2002 |
| JP | 2003042507 | 2/2003 |
| JP | 2003042509 | 2/2003 |
| JP | 2003083590 | 3/2003 |
| JP | 2003232559 | 8/2003 |
| JP | 2004005313 A | 1/2004 |
| JP | 2004053130 A | 2/2004 |
| JP | 2005040769 A | 2/2005 |
| JP | 2005177726 | 7/2005 |
| JP | 2005211319 | 8/2005 |
| JP | 2005235634 | 9/2005 |
| JP | 2006210045 | 8/2006 |
| JP | 2006522699 | 10/2006 |
| JP | 2006321721 | 11/2006 |
| JP | 2007170761 | 7/2007 |
| JP | 2007184436 | 7/2007 |
| JP | 2008125541 | 6/2008 |
| JP | 2008157548 | 7/2008 |
| JP | 2008204640 | 9/2008 |
| JP | 2010182661 | 8/2010 |
| JP | 2010239878 | 10/2010 |
| JP | 2011146137 | 7/2011 |
| JP | 2012001931 | 1/2012 |
| JP | 2012149839 A | 8/2012 |
| JP | 2013140523 A | 7/2013 |
| JP | 6159763 A | 12/2015 |
| JP | 6225858 A | 4/2016 |
| KR | 20000009824 A | 2/2000 |
| KR | 20010048235 | 6/2001 |
| KR | 20030074107 A | 9/2003 |
| KR | 20050003899 | 1/2005 |
| KR | 100771486 | 10/2007 |
| KR | 100804892 | 2/2008 |
| KR | 101102733 | 5/2011 |
| KR | 20120004243 | 1/2012 |
| KR | 101135926 | 4/2012 |
| KR | 20120039359 A | 4/2012 |
| KR | 20130108709 | 10/2013 |
| KR | 20130124184 | 11/2013 |
| WO | 0039964 | 7/2000 |
| WO | 2004037301 | 5/2004 |
| WO | 2007026387 | 3/2007 |
| WO | 2008043396 | 4/2008 |
| WO | 2008102308 | 8/2008 |
| WO | 2008120127 | 10/2008 |
| WO | 2008135093 | 11/2008 |
| WO | 2009030641 | 3/2009 |
| WO | 2009044330 A1 | 4/2009 |
| WO | 2010046875 | 4/2010 |
| WO | 2010087386 | 8/2010 |
| WO | 2010115720 | 10/2010 |
| WO | 2011033377 | 3/2011 |
| WO | 2011046875 | 4/2011 |
| WO | 2012104773 | 8/2012 |
| WO | 2012151407 | 11/2012 |
| WO | 2013014337 | 1/2013 |
| WO | 2013049297 | 4/2013 |
| WO | 2013175348 | 11/2013 |
| WO | 2015130786 | 9/2015 |
| WO | 2015200730 A1 | 12/2015 |
| WO | 2016019005 A1 | 2/2016 |

OTHER PUBLICATIONS

Wikipedia, "Home automation," Jan. 17, 2014, URL: https://en.wikipedia.org/w/index.php?title=Home_automation&oldid=591169195, retreived on Sep. 2, 2020 (11 pages).
Extended European Search Report issued in EP Application No. 17844397.4 dated Jun. 17, 2020 (8 pages).
Extended European Search report issued in EP Application No. 20152815.5 dated Aug. 4, 2020.
Klein, Laura et al., "Coordinating occupant behavior for building energy and comfort management using multi-agent systems," Automatoin in Construction, vol. 22, Mar. 2012, pp. 525-536.
First Examination Report issued in IN Application No. 201617032677 dated Jul. 30, 2020.
"Active Design Guidelines: Promoting Physical Activity and Health in Design," New York City Departments of Design and Construction, 2010.
"Assembly: Civic Design Guidelines," Center for Active Design, 2018.
Allergy Buyers Club, "Philips Wake Up Light Dawn Simulators Alarm Clocks," retrieved from http://www.allergybuyersclub.com/

(56) References Cited

OTHER PUBLICATIONS philips-wake-up-light-dawn-simulator-alarm-cloc ks.html, retrieved on Aug. 13, 2012, 2 pages.
Amendment, filed Jan. 25, 2018, for U.S. Appl. No. 15/421,046, Eisele et al., "LED Lighting System," 6 pages.
American Ultraviolet, "Handheld Germicidal Fixtures," retrieved from http://americanultraviolet.com/germicidal_solutions/commercial_products/handheld..., retrieved on Aug. 13, 2012, 1 page.
American Ultraviolet, "In Room Germicidal Solutions," HVAC MRS (0810/2.5M), retrieved from http://www.americanultraviolet.com, 2 pages.
Australian Examination report No. 1, dated Dec. 13, 2017, for Australian Application No. 2017200995, 6 pages.
Australian Patent Examination Report, dated Sep. 14, 2016, for Australian Application No. 2013308871, 5 pages.
Averett et al., "Titanium Dioxide Photocatalytic Compositions and Uses Thereof," U.S. Appl. No. 61/482,393, filed May 4, 2011, 25 pages.
Brookstone, "Tranquil Moments® Advanced Sleep Sounds," 2012, retrieved from http://www.brookstone.com/tranquil-moments-advanced-sleep-sound..., retrieved on Apr. 28, 2014, 3 pages.
Canadian Office Action, dated Jul. 18, 2017, for Canadian Application No. 2,946,367, 3 pages.
Canadian Office Action, dated Jul. 25, 2017, for Canadian Application No. 2,940,766, 6 pages.
Chinese Office Action, dated May 5, 2016, for Chinese Application No. 201380051774.0, 10 pages.
Communication pursuant to Article 94(3) EPC, dated Mar. 15, 2018, for European Application No. 15 754 628.4-1222, 9 pages.
Communication pursuant to Article 94(3) EPC, dated Nov. 23, 2016, for European Application No. 13833105.3, 8 pages.
Communication pursuant to Rule 164(1) EPC, dated Mar. 30, 2016, for European Application No. 13833105.3-1853 / 2891019, 9 pages.
Corrected Notice of Allowance, dated Jun. 26, 2017, for U.S. Appl. No. 14/012,444, Pillai et al, "Systems, Methods and Articles for Enhancing Wellness Associated With Habitable Environments," 2 pages.
Corrected Notice of Allowance, dated Jun. 6, 2017, for U.S. Appl. No. 14/012,444, Pillai et al, "Systems, Methods and Articles for Enhancing Wellness Associated With Habitable Environments," 2 pages.
Delos, "Delos and MGM Grand Las Vegas Introduce First-Ever Stay Well Rooms," Sep. 20, 2012, retrieved from http://delosliving.com/staywell/delos-mgm-grand-las-vegas-introduce-first-ever-stay-well-..., retrieved on May 14, 2014, 4 pages.
Delos, "Delos Announces First-Ever WELL™ Certified Office At CBRE Headquarters in Los Angeles," Nov. 19, 2013, retrieved from http://delosliving.com/press-release/delos-the-pioneer-of-wellness-real-estate-a nnounces-fi..., retrieved on May 14, 2014, 4 pages.
Delos, "MGM Grand and Delos Complete Expansion of Stay Well Experience and Introduce New Stay Well Lounge," Feb. 26, 2014, retrieved from http://delosliving.com/press-release/mgm-grand-and-delos-complete-expansion-of-s tay-we..., retrieved on May 14, 2014, 4 pages.
Delos, "World's First WELL® Certified Restaurants Introduced by Delos and LYFE Kitchen," Dec. 4, 2013, retrieved from http://delosliving.com/press-release/worlds-first-well-certified-restaurants-int roduced-by-d... retrieved on May 14, 2014, 4 pages.
Delos, "World's First Wellness-Infused Student Housing Model in Philadelphia for St. Joseph's University Introduced by Delos and Cross Properties," Nov. 25, 2013, retrieved from http://delosliving.com/press-release/delos-the-pioneer-of-wellness-real-estate-a nd-cross-pr..., retrieved on May 14, 2014, 4 pages.
Delos, "Introducing Wellness Real Estate—Can Your Home Actually Improve Your Health?," May 1, 2012, retrieved from http://delosliving.com/press-release/can-your-home-actually-improve-your-health/ , retrieved on May 14, 2014, 3 pages.
Eisele et al, "LED Lighting System," Notice of Allowance, dated Apr. 21, 2015, for U.S. Appl. No. 14/486,753, 9 pages.
Eisele et al, "LED Lighting System," Notice of Allowance, dated Mar. 14, 2016, for U.S. Appl. No. 14/805,243, 6 pages.
Eisele et al, "LED Lighting System," Notice of Allowance, dated May 13, 2014, for U.S. Appl. No. 13/863,589, 6 pages.
Eisele et al, "LED Lighting System," Office Action, dated Feb. 4, 2015, for U.S. Appl. No. 14/486,753, 7 pages.
Eisele et al, "LED Lighting System," Office Action, dated Jul. 26, 2012, for U.S. Appl. No. 12/900,158, 13 pages.
Eisele et al, "LED Lighting System," Office Action, dated Jun. 5, 2013, for U.S. Appl. No. 13/863,589, 6 pages.
Eisele et al, "LED Lighting System," Office Action, dated Nov. 1, 2013, for U.S. Appl. No. 13/863,589, 7 pages.
Eisele et al, "LED Lighting System," Office Action, dated Oct. 22, 2015, for U.S. Appl. No. 14/805,243, 18 pages.
Eisele et al, "LED Lighting System," Preliminary Amendment, filed Dec. 30, 2014, for U.S. Appl. No. 14/486,753.
Eisele et al, "LED Lighting System," Preliminary Amendment, filed Sep. 15, 2015, for U.S. Appl. No. 14/805,243, 9 pages.
Eisele et al, "LED Lighting System," Preliminary Amendment, filed Sep. 8, 2016, for U.S. Appl. No. 15/187,317, 9 pages.
Eisele et al, "LED Lighting System," Response, filed Jan. 27, 2014, for U.S. Appl. No. 13/863,589, 3 pages.
Eisele et al, "LED Lighting System," Response, filed Jan. 5, 2016, for U.S. Appl. No. 14/805,243, 3 pages.
Eisele et al, "LED Lighting System," Response, filed Mar. 6, 2015, for U.S. Appl. No. 14/486,753, 3 pages.
Eisele et al, "LED Lighting System," Response, filed Sep. 4, 2013, for U.S. Appl. No. 13/863,589, 3 pages.
Eisele et al., "LED Lighting System," Amendment, filed Oct. 24, 2012, for U.S. Appl. No. 12/900,158, 12 pages.
Eisele et al., "LED Lighting System," U.S. Appl. No. 61/249,858, filed Oct. 8, 2009, 58 pages.
Eisele et al., "LED Lighting System," Notice of Allowance dated Jan. 9, 2013, for U.S. Appl. No. 12/900,158, 9 pages.
European Search Report for EP Application No. 15160578.9, dated Aug. 11, 2015, 8 pages.
Examiner's Report issued in CA Application No. 2,940,766 dated Jan. 11, 2019.
Extended European Search Report and Lack of Unity of Invention Sheet B, dated Jul. 28, 2016, for European Application No. 13833105.3, 17 pages.
Extended European Search Report, dated Feb. 1, 2018, for European Application No. 17167920.2-1213, 10 pages.
Extended European Search Report, dated Jul. 12, 2017, for European Application No. 15754628.4-1958, 11 pages.
Extended European Search Report, dated May 28, 2018, for European Application No. 16737803.3-1222/3245631, 7 pages.
Extended European Search Report, dated Nov. 5, 2014, for European Application No. 12779504.5-1352, 6 pages.
Fabrictech International, "PureCare™ Antibacterial Silver," retrieved from http://www.fabrictech.com/shop/purecaresilver.html, retrieved on Aug. 13, 2012, 1 page.
Fabrictech International, "Total Health & Wellness Protection Package—Save 25%," retrieved from http://www.fabrictech.com/shop/custom-package/total-healthawellness-protection.h tml, retrieved on Aug. 13, 2012, 3 pages.
Goodman, "Green Wall Frame," Amendment After Allowance, filed May 11, 2016, for U.S. Appl. No. 29/528,147, 8 pages.
Goodman, "Green Wall Frame," Notice of Allowance, dated Feb. 11, 2016, for U.S. Appl. No. 29/528,147, 11 pges.
GSky Plant Systems, Inc., "Smart Wall Cabinet," 2012, retrieved from http://gsky.com/green-walls/smartwall/, retrieved on Apr. 29, 2015, 3 pages.
International Search Report and the Written Opinion of the International Searching Authority, dated Jun. 8, 2015, for International Application No. PCT/US2015/017528, 20 pages.
International Search Report and Written Opinion of the International Searching Authority, dated Aug. 29, 2016, for International Application No. PCT/US2016/034416, 22 pages.
International Search Report for PCT/US2017/048382 dated Jan. 4, 2018 (4 pages).
International Search Report, dated Apr. 28, 2016, for International Application No. PCT/US2016/013215, 5 pages.

(56) References Cited

OTHER PUBLICATIONS

International Search Report, dated Dec. 26, 2013, for International Application No. PCT/US2013/057070, 4 pages.
International Search Report, dated Feb. 4, 2011, for International Application No. PCT/US2010/051791, 2 pages.
Japanese Office Action dated Apr. 25, 2017 for JP Application No. 2015-529995, with English summary, 14 pages.
Jernigan, "Light studies focus on circadian rhythms," BioPhotonics, Jul. 2009, retrieved from http://www.photonics.com/Article.aspx?PID=I&VID=43&IID=396&AID=38995, retrieved on Nov. 3, 2014, 2 pages.
Jernigan, R., "Light Studies Focus on Circadian Rhythms," Photonics Showcase, Nov. 2009, p. 12.
Jones, "Chapter 4—Acoustical Treatment for Indoor Areas," in Handbook for Sound Engineers, Ballou (ed.), Burlington, MA, Focal Press, 2008, 65-94.
Land, "Using Vitamin C to Neutralize Chlorine in Water Systems," Recreation Management Tech Tips, Apr. 2005, retrieved from http://www.fs.fed.us/t-d/pubs/htm1/05231301/05231301.html, retrieved on Mar. 1, 2016, 6 pages.
Macary et al., "Systems, Methods and Articles for Monitoring and Enhancing Human Wellness," U.S. Appl. No. 15/543,114, filed Jul. 12, 2017, 113 pages.
Mold Inspection California, "Killing Mold With Ozone & Thermal Heat," retrieved from http://moldinspectioncalifornia.com/kill_mold_with_ozone.html, 3 pages.
NaturVention, "Science," URL=https://www.naturvention.com/technology-and-science/science/, download date Apr. 5, 2016, 4 pages.
NaturVention, "Technology," URL=https://www.naturvention.com/technology-and-science/, download date Apr. 5, 2016, 6 pages.
Office Action issued in CN Application No. 201580021358.5 dated Feb. 2, 2019.
Office Action, dated May 21, 2018, for U.S. Appl. No. 15/121,953, Pillai et al., "Systems and Articles for Enhancing Wellness Associated With Habitable Environments," 38 pages.
Office Action, dated May 31, 2018, for U.S. Appl. No. 15/421,046, Eisele et al., "LED Lighting System," 9 pages.
Office Action, dated Oct. 27, 2017, for U.S. Appl. No. 15/421,046, Eisele et al., "LED Lighting System," 8 pages.
OxiTitan, "Light Powered Protection," retrieved from http://www.oxititan.com, retrieved on Aug. 13, 2012, 2 pages.
Pervez et al., "Photonic Crystal Spectrometer," U.S. Appl. No. 61/278,773, filed Oct. 12, 2009, 78 pages.
Pervez et al., "Photonic Crystal Spectrometer," U.S. Appl. No. 61/349,570, filed May 28, 2010, 52 pages.
Pillai et al., "Systems, Methods and Articles for Enhancing Wellness Associated With Habitable Environments," Amendment, filed Jul. 21, 2016, for U.S. Appl. No. 14/012,444, 25 pages.
Pillai et al., "Systems, Methods and Articles for Enhancing Wellness Associated With Habitable Environments," Office Action, dated Mar. 22, 2016, for U.S. Appl. No. 14/012,444, 29 pages.
Pillai et al., "Systems, Methods and Articles for Enhancing Wellness Associated With Habitable Environments," Preliminary Amendment, filed Mar. 25, 2015, for U.S. Appl. No. 14/012,444, 149 pages.
Pillai et al., "Systems, Methods and Articles for Enhancing Wellness Associated With Habitable Environments," U.S. Appl. No. 15/409,233, filed Jan. 18, 2017, 84 pages.
Pillai et al., "Systems, Methods and Articles for Enhancing Wellness Associated With Habitable Environments," U.S. Appl. No. 15/421,022, filed Jan. 31, 2017, 84 pages.
Preliminary Amendment, filed Jul. 12, 2017, for U.S. Appl. No. 15/543,114, Macary et al., "Systems, Methods and Articles for Monitoring and Enhancing Human Wellness," 10 pages.
Summons to attend oral proceedings issued in EP Application No. 15754628.4 dated Sep. 10, 2018.
Suryadevara, N.K. et al., "Sensor data fusion to determine wellness of an elderly in intelligent home monitoring environment", Instrumentation and Measurement Technology Conference, Graz: IEEE, (20120513), ISSN 1091-5281, pp. 947-952, XP032451677.
Vitashower Corp., "Products," retrieved from http://www.vitashowercorp.com/products.html, retrieved on May 13, 2014, 8 pages.
Vitashower Corporation, "Ascorbic Acid Reduction of Residual Active Chlorine in Potable Water Prior to Halocarboxylate Determination," from Urbansky et al., Journal of Environmental Monitoring 2(3):253-256, 2000, retrieved from http://www.vitashowercorp.com/research.html, retrieved on May 13, 2014, 2 pages.
Vitashower Corporation, "Frequently Asked Questions," 2003, retrieved from http://www.vitashowercorp.com/FAQs.html, retrieved on May 13, 2014, 3 pages.
Vitashower Corporation, "Vitamin C Shower Filter SF-2000," 2003, retrieved from http://www.vitashowercorp.com/products.html, retrieved on May 13, 2014, 8 pages.
Vitashower Corporation, "Welcome to Vitashower Corporation," 2003, retrieved from http://www.vitashowercorp.com/index.html, retrieved on May 13, 2014, 4 pages.
Wikipedia, "Thermostat," as archived on Jan. 24, 2014, URL=https://en.wikipedia.org/w/index.php?title=Thermostat&oldid=592239648, download date Jun. 30, 2017, 10 pages.
Written Opinion of the International Searching Authority, dated Apr. 28, 2016, for International Application No. PCT/US2016/013215, 16 pages.
Written Opinion of the International Searching Authority, dated Dec. 26, 2013, for International Application No. PCT/US2013/057070, 5 pages.

* cited by examiner

500 ↘

| Provide signals to vary illumination passed by pane(s) of electrochromatic material | ─ 502 |

| Provide signals to control electrical motor drivingly coupled to move shade(s)/curtain(s) | ─ 602 |

FIG. 6

SYSTEMS AND METHODS FOR ENHANCING WELLNESS ASSOCIATED WITH HABITABLE ENVIRONMENTS

CROSS-REFERENCE TO RELATED APPLICATIONS

This application is a continuation of U.S. application Ser. No. 15/421,022, filed Jan. 31, 2017, which issued as U.S. Pat. No. 10,845,529 on Nov. 24, 2020, and is a continuation of U.S. application Ser. No. 15/409,233, filed Jan. 18, 2017, which is issued as U.S. Pat. No. 10,691,148 on Jun. 23, 2020, both of which are continuations of U.S. application Ser. No. 14/012,444, filed Aug. 28, 2013, which issued as U.S. Pat. No. 9,715,242 on Jul. 15, 2017, which claims the benefit of U.S. Provisional Application No. 61/694,125, filed Aug. 28, 2012, all of which are incorporated herein by reference in their entirety.

BACKGROUND

Field

This disclosure generally relates to habitable environments, for instance homes, hotel or motels, offices and hospitals, and particularly to techniques for enhancing human habitation in such environments.

Description of the Related Art

Most people spend significant amounts of time in habitable environments such as enclosed spaces associated with homes, apartments, condominium units, hotel suites or rooms, motel suites or rooms, spas, hospital, and other public and private facilities. Sometimes these enclosed spaces are controlled, or even owned by, the principal occupants, such as homes, apartments or condominium units. Other times these enclosed spaces are controlled by others, for example a facility owner or operator who may own and/or operate a hotel, motel, spa, hospital.

Significant time in these spaces exposes the occupant to a wide range of environmental factors, any of which may have either adverse or beneficial effects on the occupant's health, well-being or sense of well-being. Minimizing exposure to environmental factors that tend to have an adverse effect is desirable, as is increasing exposure to environmental factors that tend to have a beneficial effect.

New approaches that enhance habitable environments are desirable.

BRIEF SUMMARY

Various approaches described herein employ combinations of passive and active techniques for enhancing environmental characteristics of inhabitable environments, to reduce or ameliorate adverse effects and to increase beneficial effects. These approaches may have specific application in hospitality settings, for instance hotel or motel rooms, spas, resorts, cruise boat cabins, and extended stay suites. These approaches may have application in occupational environments, for instance offices, retail locations, factories or warehouses. These approaches may have application in residential settings, for instance homes, apartments, porches, condominiums or other residences. These approaches may have application in other settings, for instance hospitals or clinics, waiting areas associated with transportation such as airports and train stations, and/or public areas such as theaters, arenas, stadiums, museums and other venues. The various combinations may advantageously produce synergistic results, which may not be otherwise achievable on an individual basis.

A system to control environmental characteristics in an enclosed space may be summarized as including a control subsystem that includes at least one processor and at least one nontransitory processor-readable medium that stores at least one of processor-executable instructions or data; an illumination subsystem operable to control illumination characteristics of illumination provided in at least a portion of the enclosed spaced, the illumination subsystem including: a plurality of illumination sources selectively operable to emit illumination at a number of levels and a number of wavelengths; at least one actuator operable to control an amount of illumination received into the enclosed space via one or more windows from an external source of illumination; and at least one user actuatable input device located in the enclosed space and communicatively coupled to the control subsystem and selectively actuatable by a user to switch between a circadian setting and at least one override setting, wherein: the control subsystem is communicatively coupled to control the plurality of illumination sources and the at least one actuator, and when in the circadian setting the control subsystem provides signals to the illumination sources and the at least one actuator to cause the illumination sources and the at least one actuator to provide illumination according to a defined circadian pattern over a period of time, the circadian pattern at least approximately matching changes in illumination level and color temperature of naturally occurring illumination of at least one defined latitude over the period of time.

At least one actuator may include electrochromatic glass in the at least one window. At least one actuator may include an electric motor physically coupled to a transmission that selectively positions at least one blackout shade across the at least one window. In a night portion of the circadian pattern, the control subsystem may provide signals to at least a subset of the illumination sources which are, for example solid-state illumination sources or small incandescent lights to produce a low level of illumination proximate at least one path to a door of the enclosed space. When in a first override setting of the at least one override setting the control subsystem may provide signals to the illumination sources and the at least one actuator to cause the illumination sources and the at least one actuator to provide illumination that does not follow the defined circadian pattern. When in a second override setting of the at least one override setting the control subsystem may provide signals to the illumination sources and the at least one actuator to cause the illumination sources and the at least one actuator to provide illumination to the enclosed space based at least in part on a geographic location from where an occupant of the enclosed spaced originated to accommodate a change in circadian rhythm due to travel by the occupant. When in a third override setting of the at least one override setting the control subsystem may provide signals to the illumination sources and the at least one actuator to cause the illumination sources and the at least one actuator to provide illumination to the enclosed space based at least in part on a time of year to accommodate a change in circadian rhythm due to seasonal variation at a geographic location of the enclosed space. When in yet another override setting of the at least one override setting the control subsystem may provide signals to the illumination sources and the at least one actuator to cause the illumination sources and the at least one actuator to provide illumination to the enclosed space to produce a therapeutic effect in an occupant of the enclosed space. The system may further include at least one sensor positioned to detect presence of an occupant in the enclosed spaced and communicatively coupled to the control subsystem to provide signals indicative of a current occupancy condition of the enclosed space. The system may further include at least one user actuatable input device located remotely from the enclosed space and communicatively coupled to the control subsystem and selectively actuatable to switch between a plurality of settings for the system. The system may further include an air handling subsystem to control air characteristics of air in the enclosed space, the air handling system including at least one of: an air filter, a heater, an air conditioner, a humidifier, a dehumidifier, a vent, a fan, or a compressor, and the air handling system including at least one of: a temperature sensor or a humidity sensor positioned to detect a temperature or a humidity proximate at least one portion of the enclosed space. The control subsystem may provide signals to at least one portion of the air handling subsystem to control at least one of the temperature or the humidity of air in the enclosed space. The control subsystem may provide signals to adjust at least the temperature of the air in the enclosed space based at least in part on the circadian pattern over the period of time. The at least one air filter may include at least one of: a HEPA mechanical air filter, an electrostatic particle air filter, or an ultraviolet air filter. The air handling subsystem may further include a number of inlets for selectively introducing scents into the air in the enclosed space from a number of reservoirs and the control subsystem may provide signals to at least one portion of the air handling subsystem to control the introduction of the scents into the air in the enclosed space. The control subsystem may provide signals to at least one portion of the air handling subsystem to control the introduction of the scents into the air in the enclosed space based on a defined schedule. The control subsystem may provide signals to at least one portion of the air handling subsystem to control the introduction of the scents into the air in the enclosed space on demand in response to a user input. The system may further include a water supply subsystem including a sediment filter and an activated charcoal filter that filters water that is to be supplied to the enclosed space via a faucet or a showerhead. The water supply subsystem may further include an ultraviolet water sanitizer that illuminates water that is to be supplied to the enclosed space via a faucet or a showerhead with ultraviolet illumination. The water supply subsystem may further include an inlet to supply vitamin C to water that is to be supplied to the enclosed space via a showerhead. The system may further include an ambient sound subsystem, that may include at least one piece of acoustic insulation positioned to acoustically insulate at least some of a number of plumbing components; at least one acoustic damping door that acoustically insulates the enclosed space from an exterior thereof when the at least one acoustic damping door is in a closed position; at least one acoustic damping window that acoustically insulates the enclosed space from the exterior thereof when the at least one acoustic damping window is in a closed position; at least one acoustic damping walling component that acoustically insulates the enclosed space from the exterior thereof; and at least one acoustic damping flooring component that acoustically insulates the enclosed space from the exterior thereof. An ambient sound level in the enclosed space may be less than 45 dB when active source of sound is operating in the enclosed space. The system may further include at least one speaker communicatively coupled to be controlled by the control subsystem to play sound in the enclosed space at a sound level that changes in synchronization with a change in a level of illumination emitted by the illumination sources. The control subsystem may provide signals to gradually increase both the sound and illumination levels in response to an occurrence of a pre-set time. The system may further include a cushioned low volatile organic compound emitting flooring in the enclosed space. The system may further include a textured reflexology flooring path in the enclosed space. The system may further include at least one electromagnetic field shield positioned relative to wiring to reduce a level of electromagnetic field introduced into the enclosed space by the wiring.

A method of controlling environmental characteristics in an enclosed space may be summarized as including receiving at a first time a first input indicative of a selection of a circadian setting; in response to the first input indicative of the selection of the circadian setting, providing signals by a control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a circadian pattern; receiving at a second time a second input indicative of a selection of a first non-circadian setting; and in response to the second input indicative of the selection of the first non-circadian setting, providing signals by the control subsystem to cause a plurality of illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to the circadian pattern.

In response to the second input indicative of the selection of the first non-circadian setting, the control subsystem may provide signals to the plurality of illumination sources and the at least one actuator such that the combination of the artificial and the natural illumination remains constant over the second period of time. The method may further include receiving at a third time a third input indicative of a selection of a second non-circadian setting that is a sleep time setting; and in response to the third input indicative of the second non-circadian setting that is the sleep time setting, providing signals by the control subsystem to cause a subset of the illumination sources proximate to a floor in the enclosed space to emit artificial illumination at a low illumination level along at least one path and to cause the at least one actuator to prevent natural illumination from being received into the enclosed space via the one or more windows. The method may further include receiving at a fourth time a fourth input indicative of a selection of a travel adjustment setting; in response to the fourth input indicative of the travel adjustment setting: determining a travel adjustment illumination pattern based at least in part on a geographic location from where an occupant of the enclosed spaced originated to accommodate a change in circadian rhythm due to travel by the occupant; and providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern in the enclosed space. The method may further include receiving at a fourth time a fourth input indicative of a selection of a light therapy setting; and in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern in the enclosed space over a therapeutic period of time. Providing signals by the control subsystem to cause the at least one actuator to control at least the level of natural illumination received into the enclosed space via the one or more windows may include providing signals to vary an amount of illumination passed by at least one pane of electrochromatic material. Providing signals by the control subsystem to cause the at least one actuator to control at least the level of natural illumination received into the enclosed space via the one or more windows may include providing signals to control an electrical motor drivingly coupled to move at least one of a shade or a curtain relative to the at least one window. The method may further include detecting by at least one sensor whether the enclosed spaced is occupied; and providing signals to the control subsystem indicative of whether the enclosed space is occupied. The method may further include receiving input by at least one user actuatable input device located remotely from the enclosed space; and providing signals to the control subsystem indicative of the received input. The method may further include providing signals by the control subsystem to at least one component of an air handling subsystem to control air characteristics of air in the enclosed space. Providing signals to at least one component of the air handling subsystem may include providing signals to at least one of an air filter, a heater, an air conditioner, a humidifier, a dehumidifier, a vent, a fan, or a compressor to control at least one of the temperature or the humidity of air in the enclosed space. The method may further include receiving signals by the control subsystem from at least one of: a temperature sensor or a humidity sensor positioned to detect a temperature or a humidity proximate at least one portion of the enclosed space. Providing signals to at least one component of the air handling subsystem may include providing signals to adjust at least a temperature of the air in the enclosed space based at least in part on the circadian pattern over the period of time. The method may further include filtering air for the enclosed space with at least one of: a HEPA mechanical air filter, an electrostatic particle air filter, or an ultraviolet air filter. The method may further include providing signals by the control subsystem to selectively introduce scents into the air in the enclosed space from a number of reservoirs. Providing signals by the control subsystem to selectively introduce scents into the air in the enclosed space may include providing signals based on a defined schedule. Providing signals by the control subsystem to selectively introduce scents into the air in the enclosed space may include providing signals based on demand in response to a user input. The method may further include filtering a supply of water to a faucet or a showerhead of the enclosed space via a water supply subsystem including at least one of a sediment filter or an activated charcoal filter, and exposing the water to ultraviolet illumination to sanitize the water. The method may further include introducing vitamin C into water that is to be supplied to the showerhead of the enclosed space. The method may further include supplying signals by the controller subsystem to at least one speaker to play sound in the enclosed space at a sound level that changes in synchronization with a change in a level of illumination emitted by the illumination sources.

A system to enhance environmental characteristics in a habitable environment may be summarized as including at least one acoustic damping window that acoustically insulates the habitable environment from the exterior thereof when the at least one acoustic damping window is in a closed position; at least one acoustic damping walling component that acoustically insulates the habitable environment from the exterior thereof; at least one acoustic damping flooring component that acoustically insulates the habitable environment from the exterior thereof; and at least one speaker selectively operable to play sound in the habitable environment.

The system may further include a plurality of illumination sources selectively operable to emit artificial illumination at a number of levels and a number of wavelengths in the habitable environment; at least one actuator operable to control an amount of illumination received into the habitable environment via one or more windows from an external source of natural illumination. The system may further include a control subsystem communicatively coupled to control the plurality of illumination sources, the at least one actuator, and the at least one speaker. The system may further include at least one acoustic damping door that acoustically insulates the habitable environment from an exterior thereof when the at least one acoustic damping door is in a closed position. The system may further include a photocatalyst antimicrobial agent on at least one surface in the habitable environment.

A method of controlling environmental characteristics in a habitable environment may be summarized as including distributing an antimicrobial agent in the habitable environment prior to occupancy of the habitable environment by a first occupant; subjecting surfaces in the habitable environment to ultraviolet illumination prior to occupancy of the habitable environment by the first occupant; applying antimicrobial bedding to a bed in the habitable environment prior to occupancy of the habitable environment by the first occupant; and setting an illumination pattern that controls both artificial and natural illumination provided in the habitable environment based on at least one characteristic of the first occupant.

The method may further include setting a sound pattern that controls artificial sound provided in the habitable environment based on at least one characteristic of the first occupant. Setting a sound pattern may include setting a sound pattern that is synchronized at least in part to the illumination pattern that controls both artificial and natural illumination provided in the habitable environment based on at least one characteristic of the first occupant. The method may further include removing the antimicrobial agent from the habitable environment prior to occupancy of the habitable environment by the first occupant. Distributing an antimicrobial agent in the habitable environment may include distributing a photocatalytic antimicrobial agent; and may further include exposing the antimicrobial agent to a defined wavelength of illumination for a defined time prior to occupancy of the habitable environment by the first occupant. The method may further include providing treated water to the habitable environment.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 5 is a flow diagram that shows a low level method of operating one or more components of a habitable environment enhancement system to adjust an amount of natural light received in the habitable environment using electrochromatic panes, according to one illustrated embodiment, which may be useful in performing at least a portion of the method illustrated in FIG. 4.

FIG. 6 is a flow diagram that shows a low level method of operating one or more components of a habitable environment enhancement system to adjust an amount of natural light received in the habitable environment using drapes, shades or curtains, according to one illustrated embodiment, which may be useful in performing at least a portion of the method illustrated in FIG. 4.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with environmental control such as fans, blowers, heaters, coolers such as air conditioners or swamp coolers, compressors, and control systems such as computing systems, as well as networks and other communications channels have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Environment Overview

Figure 1:
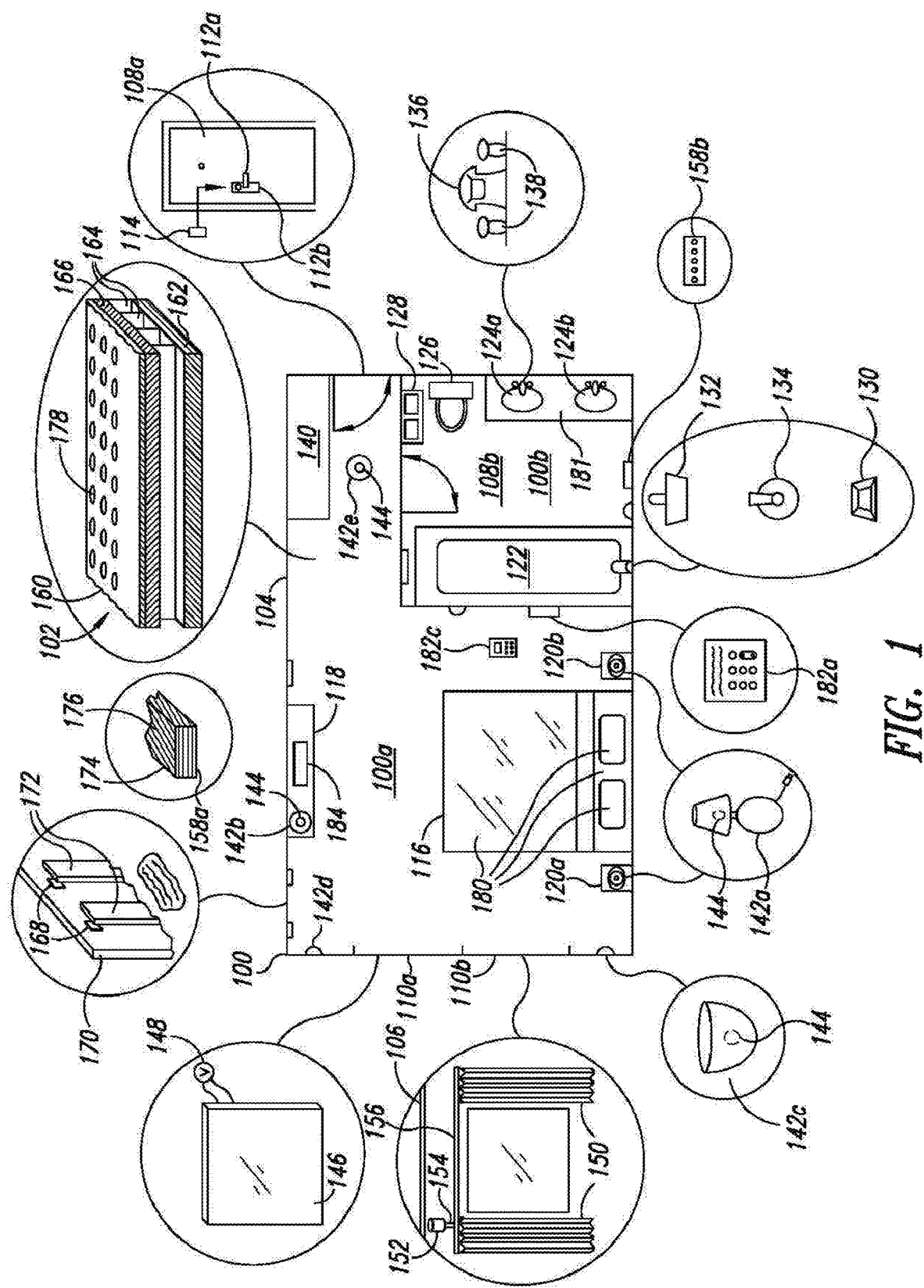
FIG. 1 is a schematic diagram of a habitable environment according to one illustrated embodiment, including enlarged views of various elements or components of the habitable environment.

FIG. 1 shows a habitable environment 100, according to one illustrated embodiment in which various apparatus, methods and articles described herein may operate.

The habitable environment 100 may take the form of one or more enclosed spaces, such as one or more rooms, for instance in a house, hotel, spa, condominium unit, apartment, office, hospital, or other accommodation which people typically inhabit.

The habitable environment 100 includes a floor system 102, wall system 104, and ceiling system 106, and may include one or more doors 108a, 108b (collectively 108) and/or windows 110a, 110b (collectively 110). The doors 108 may provide ingress and egress to an exterior environment, or may provide ingress and egress to other enclosed spaces within the habitable environment 100. For instance, one door 108a may provide passage between the habitable environment 100 and a hallway (not called out) outside of the habitable environment 100. Another door 108b may provide passage between one portion and another portion of the habitable environment 100, such as between a bedroom or living area 100a and a bathroom 100b.

The door 108a to the exterior may have a handle 112a with associated lock, for instance a cardkey entry lock 112b. Cardkey entry lock 112b reads an identifier either encoded in a magnetic stripe or in a wireless transponder (e.g., radio frequency identification or RFID transponder or smartcard) of a cardkey 114. The identifier may be logically associated with an inhabitant or occupant of the habitable environment 100. For example, a hotel guest may be assigned to a given suite, and issued a cardkey 114 that provides access to the suite. The identity of the guest may be stored in a database or other data structure with a logical relationship (e.g., key, pointer) to the suite. Likewise, various attributes of the guest may be stored in the database or other data structure, logically associated with the identity of the guest. As explained below, this may allow various aspects of the habitable environment 100 to be customized for the particular occupant.

As illustrated, the habitable environment 100 may be a suite, with a combined sleeping and living area 100*a*, and a separate bathroom 100*b*. The habitable environment 100 may include various pieces of furniture or fixtures. For example, the habitable environment 100 may include a bed 116, dresser 118, end tables 120*a*, 120*b* (collectively 120). Also for example, the habitable environment 100 include a bathtub or shower 122, sinks 124*a*, 124*b* (collectively 124), commode 126 and optionally towel racks 128 in the bathroom portion 100*b*. The bath or shower 122 may have a faucet 130, showerhead 132 and control handle 134. The control handle 134 is operable to control a flow of water via the faucet 130 and/or showerhead 132, from a supply of water (not shown in FIG. 1). The sink(s) may have a faucet 136 and control handle(s) 138. The control handle(s) 138 is operable to control a flow of water via the faucet 136 from a supply of water (not shown in FIG. 1). The habitable environment 100 may additionally include one or more closets 140.

The habitable environment 100 may include a number of components (e.g., devices, articles, structures) which contribute to a wellness or sense of wellness of the occupant of the habitable environment 100. Some of these components are active components, driven in response to commands or signals, while other components are passive components. These components are brought together as a system, in order to provide synergistic results, thereby enhancing a health, wellness or sense of wellbeing of an inhabitant or occupant of a habitable environment or enclosed space. The various components are discussed below with reference to FIGS. 1 and 2, and exemplary operation of such are discussed below with reference to FIGS. 3-10.

The habitable environment 100 may include a number of active components operable to achieve desired environmental characteristics, for example related to illumination, heating, ventilation and air conditioning (HVAC), water treatment, and acoustics.

Controlled lighting or illumination is one aspect of achieving the desired environmental characteristics of the habitable environment 100. Thus, the habitable environment 100 may include a number of artificial luminaires 142*a*-142*e* (collectively 142), which are controlled to produce desired output, for example by varying intensity and/or composition of wavelengths or color. Luminaires 142 may take a variety of forms, for example lamps (e.g., tabletop, floor standing) 142*a*, 142*b*, sconces 142*c*, 142*d*, and/or overhead lighting 142*e*. The luminaires 142 may employ a variety of illumination sources 144, for example incandescent lights, florescent lights, compact florescent lights, and light emitting diode (LED) lighting. The luminaires 142 may optionally include ballasts (e.g., electronic ballasts) and/or other electrical or electronic components required for operation. The luminaires 142 may also include various passive and/or active thermal management components to remove heat, thereby prolonging the operational life of the luminaires 142. Each luminaire 142 may include a plurality of individual illumination or light sources 144, respective ones or sets of the illumination sources 144 operable to emit light in a respective range of wavelengths. Some of the ranges may overlap, while other ranges may or may not overlap. The ones or sets of the illumination sources 144 may be individually operable to achieve any desired distribution of wavelengths at any given time. Each luminaire 142 may include one or more intensity adjustment circuits (e.g., dimmer circuits), which may take a large variety of forms depending on the type of illumination sources 144 employed. For example, an adjustable resistance type dimmer switch may be employed with incandescent sources, while a more sophisticated pulse width modulation technique may be used to control intensity of LED sources.

The habitable environment 100 may additionally or alternatively include a number of components which are controlled to adjust natural light being received in the habitable environment 100 via one or more windows 110 from an exterior thereof for example from a natural source of light (e.g., the Sun). These may include electrochromatic panes 146 in the window 110*a* and associated actuator, for instance a voltage source 148 coupled to control a transmissivity of the electrochromatic panes 146. Electrochromatic panes 146 may commonly be referred to as electrochromatic glass, but the embodiments herein are not intended to be limited to glass. These may include one or more drapes, shades or curtains or other window coverings (collectively window covering 150) and an actuator such as an electric motor 152 coupled by a transmission 154 to drive the window covering along a track 156 relative to the window(s) 110*b*.

Various approaches to illumination and components to provide illumination are discussed below, with reference to FIGS. 2 and 4-6.

HVAC is another aspect by which the desired environmental characteristics of the habitable environment 100 may be achieved. Thus, the habitable environment 100 may include a number of vents 158*a*-158*b* (only three shown, collectively 158) that provide air to the habitable environment 100 or portions thereof having desired air temperature, humidity, and/or air quality. At least one of the vents 158 may selectively supply scent(s) to the habitable environment 100 or a portion thereof. Various air treatments and components for treating air are discussed below, with reference to FIGS. 2 and 7.

Likewise, water is yet another aspect by which the desired environmental characteristics of the habitable environment 100 may be achieved. Thus, the habitable environment 100 may include a number of faucets 130, 136 and/or showerheads 132 which supply water which has been treated in a variety of ways to enhance wellness. Various water treatments and components for treating water are discussed below, with reference to FIGS. 2 and 9.

The habitable environment 100 may include a number of passive components to achieve desired environmental characteristics, for example related to flooring system 102, wall system 104, ceiling system 106, acoustics, air quality (e.g., zero or low VOC emitting), and hygiene or sanitation (e.g., anti-pathogen). Many of these are discussed below.

The habitable environment 100 may include flooring system 102, wall system 104 and/or ceiling system 106 designed to achieve a variety of benefits. For example, the flooring system 102, wall system 104 and/or ceiling system 106 designed to reduce exposure to noise.

Loud environments have become a part of modern life. Fans, overhead planes, passing traffic, and loud neighbors all contribute to ambient noise conditions in the home. About half of Americans live in areas where background noise is above 55 decibels (dB)—a level that most consider bothersome. On the logarithmic decibel scale, 0 dB is the point where sounds become discernible to the human ear, and every increase of 10 dB increases the sound pressure level by a factor of 10. Regular exposure to 85 dB for over eight hours at a time can lead to permanent hearing loss. In outdoor urban spaces not immediately adjacent to any sound generators the background noise is often close to 40 db. The World Health Organization recommends an ambient sound level of under 45 dB inside homes and 30 dB for bedrooms.

Thus, the habitable environment 100 may include various passive approaches to achieve the benefit of reduced noise.

Much of the bothersome noise in homes originates from the outside, so acoustic barriers are an important part of overall sound balance. Many of the same technologies that provide effective thermal insulation in walls and windows concurrently block noise. This allows for acoustic protection solutions, while incurring little additional cost. In addition, floor lining reduces sound transmission between apartments and improves perceptions of privacy.

For example, the habitable environment 100 may include a flooring system 102 designed to achieve a variety of benefits. The flooring system 102 may include floor covering 160, subflooring 162, and optionally acoustically damping floor mounts 164 coupling the flooring 160 to the subflooring 162. The flooring system 102 may include one or more additional layers of flooring 166, which provides a resilient member or layer(s) (e.g., cork), as discussed below. The flooring system 102 may include baffle material or insulation (not illustrated), for instance between the additional layer of flooring 166 and the subflooring 162. The flooring system 102 may additionally or alternatively include pads or sheets of material (not shown) that acoustically isolate sources of vibration (e.g., vibrating appliances such as washing machines).

The flooring system 102 uses non-toxic, natural materials that are intended to absorb the sound of footfalls and other vibrations, and provide isolation from exterior or interior sound.

Also for example, the habitable environment 100 may include a wall system 104 designed to achieve acoustic damping. The wall system 104 may include specially constructed walls which incorporate resilient channels 168, double-wallboard or sheetrock 170, double-studs 172, and acoustic insulation designed to decrease sound transmission. The resilient channels 168 resilient couple the double-wallboard or sheetrock 170 to the double-studs 172 to reduce transmission of vibration.

As another example, the habitable environment 100 may employ acoustically damping doors 108. For instance, solid oak doors that tightly seal to a door frame, may achieve sound reduction on par with well-constructed walls.

As a further example, the habitable environment 100 may employ acoustic damping windows 110. For instance triple glazed windows 110 with vacuum or rare earth gases trapped therebetween may minimize sound transmission from the exterior.

As yet a further example, the habitable environment 100 may employ acoustically damping plumbing insulation 174. For instance, non-toxic blankets of acoustically damping material 174 may be wrapped around water pipes (not shown) and air ducts 176 to reduce the sound transmitted by metal conduits.

The health effects of flooring have become the focus of a growing number of studies. Research shows that standing on surfaces without any give or cushioning for extended periods of time forces muscles into a constant state of flexion. This decreases circulation, promotes bad posture, causes lower back pain and can lead to orthopedic ailments. Cushioned mats decrease the impact on joints and promote muscle relaxation.

The habitable environment 100 may employ a cushion-lined flooring system 102 in order to realize a number of benefits, including increased circulation and promotion of healthy posture. The result may be fewer reports of joint pain, discomfort, and low energy. In addition, standing on softer surfaces decreases the risk of developing plantar fasciitis, and can alleviate symptoms for those already suffering from the condition. The flooring system 102 should be soft or resilient enough to allow for underfoot comfort, yet strong enough to improve lumbar support. The flooring system 102 consists of floating construction, for example with cork under layer(s) 166 to reduce forces generated from impacts by increased deflection.

Reflexology is a traditional practice of massage, which aims to reduce the symptoms of various ailments. Practitioners use stimulation of specific areas of the hands and feet to reduce tension and stress. Evidence has shown that the practice of reflexology has powerful anxiety reduction with reduced blood pressure and pulse rates. The habitable environment 100 may employ a custom-designed pathway (e.g., bathroom pathway), with textured floor covering 178, designed to improve blood circulation and general wellbeing by encouraging reflexology therapy.

Due to large surface area, floor finishing can often be a major source of VOCs. The habitable environment 100 uses natural flooring materials chosen to reduce the emissions of harmful indoor air pollutants and volatile organic compounds.

Electromagnetic fields (EMF) are created when charged particles are in motion. The movement of electrical charge through wires and appliances creates electromagnetic fields. The strength of the electric field depends on the voltage (e.g. typically 120 V for households) and is present near live wires, whether or not an electrical appliance is in use. Research suggests that long-term and significant occupational exposure to EMF may increase the risk of both Alzheimer's disease and breast cancer.

Thus, EMF shielding is incorporated into the habitable environment 100. The EMF shields are designed to block the spread of the field by creating a barrier composed of conductive or magnetic materials. EMF shields have traditionally been made out of solid metal, though this poses challenges regarding weight, corrosion, and malleability. Treated metal mesh or screens with openings smaller than the electromagnetic wavelength may provide a more practical solution.

Thus, for example the habitable environment 100 may include EMF shielding for wiring. In particular, wiring may be insulated with foil wraps designed to shield EMF from occupied parts of the habitable environment 100. Also for example, low EMF electrical wiring may be employed.

Another passive approach takes advantage of anti-bacterial or anti-pathogen (i.e., "treated") materials to reduce or eliminate the presence of bacteria or pathogens. The anti-bacterial or anti-pathogen materials may be incorporated into or deposited on bedding (e.g., sheets, bedspreads, throws, pillows, pillow covers) 180, window coverings (e.g., drapes, shades, curtains) 150 and/or surfaces (e.g., counters 181, tubs or shower stalls 122, table tops 120, walls 104). For example, various materials may be impregnated or coated with anti-bacterial or anti-pathogen materials. These materials may have opening or pore sizes on the order of 1 micron, providing an effective barrier against penetration by various undesirable particles. Any seams in the bedding should be sealed. At least in the case of bedding, these materials preferably completely encase or envelope mattress, box springs, pillows, and/or comforters. Such may provide protection against bedbugs, allergens, and/or dust mites.

Examples of suitable materials may contain or include, silver (Ag) in ionic form, which has proven effective against a variety of pathogens.

In order to reduce exposure to pathogens and toxins without excessive use of chemicals or cleaning, the amenities below lower the effort required in maintaining a healthy environment.

As a further example, titanium dioxide nanoparticles have emerged as an effective means of reducing air pollutants through a photocatalyst which creates a self-cleaning surface powered by ambient light exposure. For example, the nanoparticles may catalyze a reaction converting VOCs to harmless carbon dioxide. Such may be incorporated into a photo-catalytic coating which may be used on walls to break down bacteria, virus, and VOCs when exposed to light.

The habitable environment 100 may include anti-bacterial or anti-pathogen materials as structural materials. For example, cedar may be employed in closets and/or used as baseboards. Certain species of cedar act as a natural pest control, repelling many insects. Oils present in cedar wood have been shown to repel fungi (such as mold), bacteria, insects, termites, and ticks.

An ability to control a function or operation of at least the active components may be useful in realizing the amenities and benefits offered in the habitable environment 100. Thus, a number of user operable input/output (I/O) devices, controls, panels or kiosks 182 may be supplied.

For example, an in-room user operable I/O panel 182a may include a display (e.g., LCD) to display information. The in-room user operable I/O panel 182a may include user actuatable controls (e.g., user selectable icons displayed on touch screen, keys, buttons) manipulation of which allows a user, for instance an occupant of the habitable environment 100, to select parameters or programs to execute to control one or more of the environmental characteristics of the habitable environment 100.

Also for example, a mobile or handheld device 182b may serve as an I/O device. The mobile or handheld device 182b may include a display (e.g., LCD) to display information and user actuatable controls (e.g., user selectable icons, keys, buttons) manipulation of which allows a user, for instance an occupant of the habitable environment 100 or facility personnel, to select parameters or programs to execute to control one or more of the environmental characteristics of the habitable environment 100. The mobile or handheld device 182b may be owned by the end user, for example the occupant. The mobile or handheld device 182b may execute a downloaded customized application or "APP" that communicatively interfaces via a wireless protocol (e.g., IEEE 802.11, BLUETOOTH®, WI-FI®).

Alternatively or additionally, a remote user operable I/O controls, panel or kiosk 182c (FIG. 2) may include a display (e.g., LCD) to display information. The remote user operable I/O controls, panel or kiosk 182c may include user actuatable controls (e.g., user selectable icons displayed on touch screen, keys, buttons) manipulation of which allows a user, for instance personnel of the facility in which the habitable environment 100 is located, to select parameters or programs to execute to control one or more of the environmental characteristics of the habitable environment 100.

Information about the amenities and benefits afforded by the wellness system in the habitable environment 100 may be useful in realizing the benefits of such. Information may be provided via a server and presented via a variety of devices. For instance, information may be presented via a television 184 for instance on a dedicated channel, via in-room or other display, panel or kiosk 182a, via handheld device 182b, etc.

System and Subsystems

Figure 2:
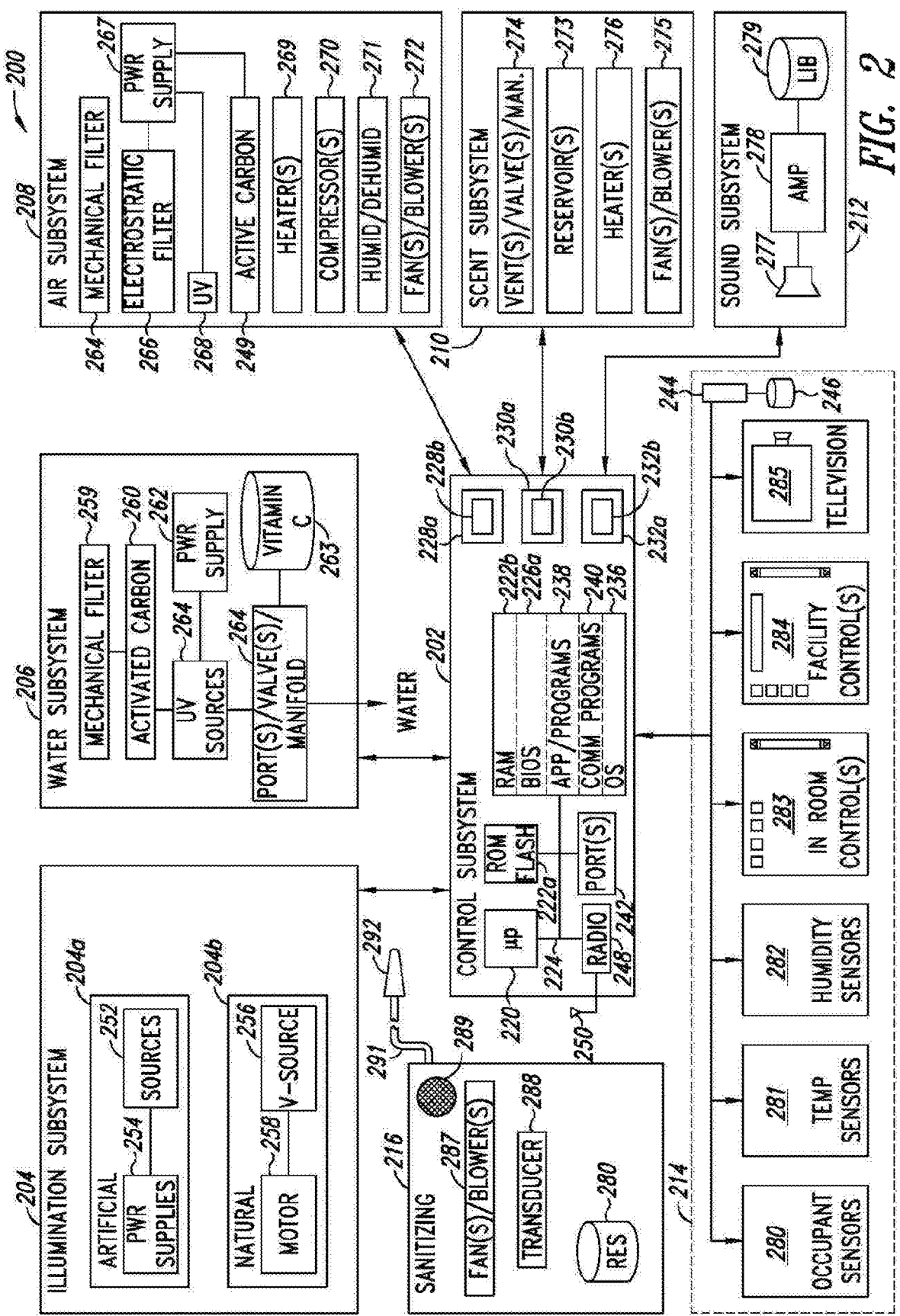
FIG. 2 is a block diagram that shows a portion of a habitable environment enhancement system to enhance a habitable environment, according to one illustrated embodiment.

FIG. 2 shows an active portion of an environmental control system 200 for controlling environmental characteristics of a habitable environment 100 (FIG. 1), according to one illustrated embodiment. FIG. 2 provides a more detailed representation of some of the components of FIG. 1.

The active portion of an environmental control system 200 includes a number of subsystems. For example, the active portion may include a control subsystem 202, illumination subsystem 204, water treatment subsystem 206, air treatment subsystem 208, scent subsystem 210, sound subsystem 212 input/output (I/O) subsystem 214. The active portion may optionally include a sanitizing subsystem 216, which as described below may be either build in or a fixture of the habitable environment 100, or may be portable, being located in the habitable environment 100 only during use. Each of the subsystems 202-216 and/or components are discussed in turn below with reference to FIG. 2. Operation of many of these subsystems 202-216 and/or components are discussed with reference to FIGS. 3-10 below.

The control subsystem 202 may take the form of a programmed computer or other processor-based system or device. For example, the control subsystem 202 may take the form of a conventional mainframe computer, minicomputer, workstation computer, personal computer (desktop or laptop), or handheld computer.

The control subsystem 202 may include one or more processing units 220 (one illustrated), nontransitory system memories 222a-222b (collectively 222) and a system bus 224 that couples various system components including the system memory 222 to the processing unit(s) 220. The processing unit(s) 220 may be any logic processing unit, such as one or more central processing units (CPUs), digital signal processors (DSPs), application-specific integrated circuits (ASICs), field programmable gate arrays (FPGAs), programmable logic controllers (PLCs), etc. Non-limiting examples of commercially available computer systems include, but are not limited to, an 80×86, Pentium, or i7 series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. The system bus 224 can employ any known bus structures or architectures, including a memory bus with memory controller, a peripheral bus, and a local bus. The system memory 222 includes nontransitory Flash or read-only memory ("ROM") 222a and nontransitory random access memory ("RAM") 222b. A basic input/output system ("BIOS") 226a, which can form part of the ROM 222a or RAM 222b, contains basic routines that help transfer information between elements within the control subsystem 202, such as during start-up.

The control subsystem 202 may include a hard disk drive 228a for reading from and writing to a hard disk 228b, an optical disk drive 230a for reading from and writing to removable optical disks 230b, and/or a magnetic disk drive 232a for reading from and writing to magnetic disks 232b. The optical disk 230b can be a CD/DVD-ROM, while the magnetic disk 232b can be a magnetic floppy disk or diskette. The hard disk drive 228a, optical disk drive 230a and magnetic disk drive 232a may communicate with the processing unit 220 via the system bus 224. The hard disk drive 230a, optical disk drive 230a and magnetic disk drive 232a may include interfaces or controllers (not shown) coupled between such drives and the system bus 224, as is known by those skilled in the relevant art. The drives 228a, 230a and 232a, and their associated computer-readable storage media 228b, 230b, 232b, may provide nonvolatile and non-transitory storage of computer readable instructions, data structures, program engines and other data for the environmental control system 200. Although control subsystem 202 is illustrated employing a hard disk 228a, optical disk 230a and magnetic disk 232a, those skilled in the relevant art will appreciate that other types of computer- or processor-readable storage media that can store data accessible by a computer may be employed, such as magnetic cassettes, flash memory, digital video disks ("DVD"), Bernoulli cartridges, RAMs, ROMs, smart cards, etc. The hard disk 228a may, for example, store instructions and data for controlling the other subsystems, for example based on specific aspects or characteristics of an occupant of the habitable environment 100 (FIG. 1), to provide environmental characteristics that promote the wellness or wellbeing of the occupant(s). The hard disk 228a may, for example, store instructions and data for presenting information about the various attributes and benefits provided by the active and passive components or measures, and instructions on how to use the environmental control system 200 and the passive components to maximize enjoyment, comfort, and wellbeing.

Program engines can be stored in the system memory 222b, such as an operating system 236, one or more application programs 238, other programs or engines and program data. Application programs 238 may include instructions that cause the processor(s) 220 to automatically generate signals to control various of the other subsystems to achieve various environmental characteristics in the habitable environment 100 (FIG. 1), for example based on one or more aspects, characteristics or attributes of an occupant thereof. Application programs 238 may include instructions that cause the processor(s) 220 to automatically receive input and/or display output via various user operable input/output (I/O) devices, controls, panels or kiosks 182 or television 184.

Other program engines (not specifically shown) may include instructions for handling security such as password or other access protection and communications encryption. The system memory 220 may also include communications programs 240, for example, a server for permitting the control subsystem 202 to provide services and exchange data with other subsystems or computer systems or devices via the Internet, corporate intranets, extranets, or other networks (e.g., LANs, WANs), as well as other server applications on server computing systems such as those discussed further herein. The server in the depicted embodiment may be markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers are commercially available such as those from Microsoft, Oracle, IBM and Apple.

While shown in FIG. 2 as being stored in the system memory 222b, the operating system 236, application programs 238, other programs/engines, program data and communications applications (e.g., server, browser) 240 can be stored on the hard disk 228b of the hard disk drive 228a, the optical disk 230b of the optical disk drive 230a and/or the magnetic disk 232b of the magnetic disk drive 232a.

An operator can enter commands and information (e.g., configuration information, data or specifications) into the control subsystem 202 via various user operable input/output (I/O) devices, controls, panels or kiosks 182 or television 184, or through other input devices such as a dedicated touch screen or keyboard (not shown) and/or a pointing device such as a mouse (not shown), and/or via a graphical user interface. Other input devices can include a microphone, joystick, game pad, tablet, scanner, etc. These and other input devices are connected to one or more of the processing units 220 through an interface such as a serial port interface 242 that couples to the system bus 224, although other interfaces such as a parallel port, a game port or a wireless interface or a universal serial bus ("USB") can be used. A monitor or other display device is coupled to the system bus 224 via a video interface, such as a video adapter (not shown). The control subsystem 202 can include other output devices, such as speakers, printers, etc.

The control subsystem 202 can operate in a networked environment using logical connections to one or more remote computers and/or devices as described above with reference to FIG. 1. For example, the control subsystem 202 can operate in a networked environment using logical connections to one or more other subsystems 204-214, one or more server computer systems 244 and associated nontransitory data storage device 246. The server computer systems 244 and associated nontransitory data storage device 246 may, for example, be controlled and operated by a facility (e.g., hotel, spa, apartment building, condominium building, hospital) in which the habitable environment 100 (FIG. 1) is located. Communications may be via wired and/or wireless network architectures, for instance, wired and wireless enterprise-wide computer networks, intranets, extranets, and the Internet. Thus, the control subsystem 202 may include wireless communications components, for example one or more transceivers or radios 248 and associated antenna(s) 250 for wireless (e.g. radio or microwave frequency communications, collected referred to herein as RF communications). Other embodiments may include other types of communication networks including telecommunications networks, cellular networks, paging networks, and other mobile networks.

Illumination (e.g., electromagnetic radiation or energy with wavelengths in the visible, near infrared (NIR) and/or near ultraviolet (NUV or UVA) portions of the electromagnetic spectrum) can have a significant effect on human health. As used herein and in the claims, the terms illumination or light include energy in the portions of the electromagnetic spectrum which are visible to humans (e.g., approximately 400 nm-approximately 700 nm) and not visible to humans (e.g., NIR or UVA). Light influences the human body in a number of unconscious ways. Metabolism has been deeply linked to the daily solar cycle through melatonin and the endocrine system. This cycle in the human body is called the circadian rhythm. Humans and animals have an internal clock that keeps the body on an approximately 24-hour cycle which matches the Earth's daily solar cycle, even in continuous darkness. Multiple bodily processes, from periods of alertness and sleep to digestion efficiency, are partially regulated by the intensity and color of light received by the eyes. However, light adjusts this internal timing to align the person to the Earth's daily solar cycle. Exposure to light comparable to the intensity of direct sunlight light will aid in resetting the circadian rhythm if it has been upset by shift work or long distance travel.

The intensity and color of light impacts different systems of the body. For example, blue light impedes the body's production of melatonin, a chemical messenger used to induce sleep. High intensities in the evening delay sleep, while light in the morning aids in waking. The appropriate brightness and color also contribute to alertness and concentration throughout the day. Melatonin is a natural antioxidant and counteracts the cancer-causing tendencies of free radicals. As a result, melatonin depletion from inappropriate exposure to bright lights leads to an increased risk of cancer. Bright light during midday and dimmer light at dinnertime aid in the digestion of carbohydrates.

Additionally, many individuals suffer from light-related mood irregularities, such as Seasonal Affective Disorder (SAD). Proper exposure to specific types of light at specific times addresses these irregularities. Exposure in the morning to gradual light brightening through dawn simulation has been shown to reduce depression. Daylight aids in the healthy development of eyesight. Myopia in children has been linked with low exposure to daylight and conversely, high reliance on dim artificial light. Age related macular degeneration, or the deterioration of eyesight with age, particularly in seniors with blue eyes can be minimized by reducing the exposure to high color temperature.

The illumination subsystem 204 may also be controlled to deliver light therapy, with or without topical photoactive substances. Such may, for example be used to treat a variety of conditions, for instance Seasonal Affective Disorder (SAD). People who live in high latitudes often experience depression during the winter as a result of long periods of reduced sunlight, a condition identified as SAD. For those affected by SAD, measures of sleep efficiency in the winter are noticeably different than those in the summer. Light therapy may be especially effective at treating SAD, producing results comparable to treatment with medication.

Another condition or syndrome commonly referred to as "jet lag" results from the relative shift between the circadian rhythm and the daily solar cycle. The effects are a disruption of sleep and a significant deterioration in mood, concentration, and cognitive performance. Controlled light exposure to help match the solar and circadian light cycles can help alleviate these symptoms.

In some individuals, the body's production or interpretation of melatonin slightly varies relative to the solar cycle, resulting in a set of symptoms identified as Delayed Sleep-Phase Syndrome (DSPS). Approximately one tenth of all adolescents and some adults find themselves falling asleep two to six hours after conventional bedtime. If left undisturbed, these individuals will often sleep soundly for approximately eight hours before waking in the middle of the day. Controlled lighting may help treat DSPS.

Emerging research indicates that different brain activity occurs when the human body is exposed to different parts of the light spectrum. Color can subconsciously affect people's abilities to do different types of tasks. For example, in one study, participants performed analytical tasks better in red light, and were more creative in blue-colored environments. Research into workplace environments has found that people in brightly colored offices had higher measured emotional status than those in subdued or neutral surroundings. On the other hand, studies have shown that intense colors may be irritating to certain individuals. Chromotherapy employs illumination of certain wavelengths or combinations of wavelengths as an effective manipulator of mood given individual preferences. Practitioners use this therapy to address issues such as meditation, intuition, speech, nervousness and anxiety.

The illumination subsystem 204 may be operated to provide dynamic custom coloring throughout the habitable environment 100 (FIG. 1) or a portion thereof in order to provide chromotherapy. Additionally, the habitable environment 100 (FIG. 1) may optionally employ a chromotherapy wall wash in the form of a wall colored by light (e.g., via cover lights or sconces) that dynamically changes color to create a desired light spectrum for different settings and times of day. Additionally or alternatively, chromotherapy lighting can be added to specific areas where colored lights may be more desirable, such as meditation spaces and steam showers.

The illumination subsystem 204 discussed below is used to preserve and remediate the disruption of circadian rhythm, enhancing health, including the natural sleep cycle, the healthy development of the eyes among some attributes, and treating or alleviating the symptoms of various disorders, syndromes and/or afflictions. The illumination subsystem 204 may, for example, expose occupants or residents of a habitable environment 100 (FIG. 1) or a portion thereof to short periods of intense artificial light for therapeutic effects while subjects are awake as part of delivering light therapy.

The illumination subsystem 204 includes an artificial illumination subsystem 204a and a natural illumination subsystem 204b, which are operated in tandem to provide desired illumination in the habitable environment 100 (FIG. 1). In particular, the illumination subsystem 204 provides lighting in the habitable environment 100 (FIG. 1) with gradually adjusted color temperature and intensity to, for example improve circadian rhythm. As discussed below, the illumination subsystem 204 may implement a dawn simulator to gradually increase light and sound levels, which are designed to awaken the body when it enters a light stage of sleep. Such may replace standard alarm clocks producing a more natural environment to slowly wake from. Such may be realized by slow opening blackout shades or slowly allowing more light to pass through an electrochromatic pane over a wakeup period. Active sound may also be slowly increased in volume. Sounds may be those found in the natural environment or may be other sounds, such as music. Such may be realized in an integral unit, or via a dedicated bedside unit, which may provide for sounds as well as artificial lighting.

Also as discussed below, the illumination subsystem 204 may implement nightlights, employing dim (e.g., low-wattage) long wavelength LED or incandescent luminaires that engage in response to motion or ambient light levels, and are designed to sufficiently illuminate rooms for safe navigation without disturbing melatonin levels.

The artificial illumination subsystem 204a includes a plurality of illumination sources 252, and optionally one or more power supplies 254. As previously noted, the illumination sources 252 may take a wide variety of forms, for instance incandescent, florescent, compact florescent, or LED lights. LED lighting may be preferable since such is extremely energy efficient and may have a long operating life. The illumination sources 252, either alone or in combination, should be capable of selectively providing a broad range of intensities and a broad range of wavelengths. Such allows the illumination sources 252 to be selectively controlled to produce a wide variety of artificial illumination conditions, for instance conditions that mimic natural light, diurnal light patterns, circadian light patterns, light therapy patterns, and/or light patterns to accommodate for changes in location (e.g., latitude and/or longitude) or changes in season (e.g., spring, summer, autumn, winter). A circadian light pattern may be a pattern of light during a defined period of time (e.g., solar day, approximately 24 hours) which mimics the intensity and/or color of naturally occurring light (e.g., sunlight and darkness) for a given location (e.g., latitude and/or longitude) and/or at a given time of year (e.g., season, month). A produced or generated or provided circadian light pattern may be produced by a combination of artificial and naturally occurring light, which may be controlled to produce a defined or desired circadian light pattern. The defined or desired circadian light pattern may itself be different from a naturally occurring circadian light pattern at a particular location and/or time of year, or may simply be shifted relative to the naturally occurring circadian light pattern at a particular location and/or time of year. The illumination sources 252 may take the form of arrays of LEDs, each LED capable of producing one or more ranges of wavelengths. Wavelength of emitted light may be adjusted by varying a drive current supplied to LEDs. Thus, desired wavelengths may be achieved by selectively operating certain sets of LEDs (e.g., LEDS that emit in a given range of wavelengths), and/or by varying a current level supplied to any given LEDs. Intensity may be adjusted by selectively operating more or less LEDS, or by controlling power supplied to one or more LEDs via the power supply or supplies 254. For example, a duty cycle of a pulse width modulated (PWM) drive signal may be varied to adjust intensity out the output.

The power supply or supplies 254 may take a wide variety of forms, mostly dependent on the source of power (e.g., AC line current, DC), and the illumination sources (e.g., LEDs). The power supply or supplies 254 may include a transformer to electrically isolate the rest of the circuit from the source of power, and/or step down or step up a voltage. The power supply or supplies 254 may include a switch mode converter, operable to step down and/or step up a voltage. The power supply or supplies 254 may include one or more rectifiers (e.g., passive diode bridge, active transistor bridge of MOSFETs or IGBTs) to rectify AC power to DC power. Less likely, the power supply or supplies 254 may include one or more inverters, to invert DC power to AC power. The power supply or supplies 254 may include one or more dedicated power supply controllers, for instance a microcontroller such as a microprocessor, DSP, ASIC, PGA, or PLC and/or associated nontransitory computer- or processor-readable media. The power supply or supplies 254 is or are communicatively coupled to control a supply of electrical power to the illumination sources.

The natural light subsystem 204b may include one or more actuators, which are drivingly coupled to control an amount of natural light received in the habitable environment 100 (FIG. 1) via one or more windows 110. As previously discussed, the actuators may, for example take the form of an electrical power source 256 coupled to control a transmissivity of one or more electrochromatic panes or panels 146 (FIG. 1). As also previously discussed, the actuators may, for example take the form of an electric motor 258, solenoid or other element drivingly coupled that control a position of one or more window coverings 150 (FIG. 1) relative to the window, and thereby adjusting an amount of illumination that passes. The window coverings 150 may take the form of "blackout shades", that are automatically operated to shield an occupant or resident of the habitable environment 100 (FIG. 1) from outdoor light. The actuator 256, 258 may receive electrical power from a voltage source, or may receive control signals from a microcontroller. Electrochromatic panes or panels 146 (FIG. 1) may be capable of adjust (i.e., selectively substantially passing, selectively substantially blocking) ranges of wavelengths passed or block, as well as intensity of natural illumination passed or blocked. Thus, electrochromatic panes or panels 146 (FIG. 1) may be preferred over the window covering approach.

Controlling ingress of ambient light (e.g., sunlight, light from street lamps, buildings or signage, security lighting) from an exterior environment aids in management of exposure to levels of light in order to help maintain healthy circadian rhythms. This is particularly important during early summer mornings and long summer evenings, particularly at high latitudes (e.g., above or greater than approximately 40 degrees North or South) and/or urban environments.

Municipal water systems use many methods to control the purity of water. Although these methods generally succeed in bringing contaminant levels within national and state limits, water quality occasionally becomes an issue. For example, the Las Vegas sodium and sulfate levels in water would fail NYC city standards. In New York, byproducts formed by chlorination are near the federal limit. In response to these concerns, habitable environments 100 may use supplemental treatment technologies to bring contaminant concentrations well within the safety limits set by American regulatory agencies, as well as international safety standards.

New York City water is currently unfiltered, but a filtration plant is under construction for water drawn from the Croton Reservoir. Additionally, a UV sanitization facility is under construction for germicidal irradiation for the remaining water sources (Catskill/Delaware system).

Sediments-Solids of sulfates and chlorides can be suspended in water and produce a cloudy opacity, or turbidity. Water with high turbidity is not inherently unhealthy but elevated levels may be indicative of problems in the filtration process, which may imply that other contaminants have not been adequately removed. The coarse filters 259 reduce suspended solids in water. This is often the first stage of treatment, which optimizes performance of subsequent filters in the system.

Municipal water systems often add chlorine-based disinfectants to the water supply to remove bacteria. This affects water odor and taste, and causes potential irritation of the eyes. The human body contains beneficial symbiotic bacteria, which are necessary for the proper function of the skin and digestive tract. These microbes on the skin are harmed by chlorine. When chlorinated water comes into extended contact with organic matter, byproducts such as tri-halomethanes and halo-acetic acids can form, which are carcinogenic.

Pharmaceuticals and Personal Care Products (PPCP) comprise a myriad of different chemicals used as active ingredients in medications, cleaning products, and health supplies. PPCP enter the water system through multiple pathways, such as incomplete metabolism of drugs in the body, improper disposal of pills or personal care and cleaning products. Potentially unsafe levels of PPCP have accumulated in lakes and rivers, where they can enter municipal water systems. PPCPs are the likely cause of hermaphroditism in fish and lake amphibians, as well as other reproductive harm. Further contamination of water supplies is expected and increases in the quantity of PPCPs in the water are the subject of numerous research programs. The activated carbon water filters 260 that reduce disinfectant byproducts, pesticides, dissolved gases, chlorine, chloramine, and some pharmaceutical and personal care products, resulting in cleaner and better-tasting water. "Activated" charcoal filters contain a maze of passageways and openings, giving activated carbon some 1000 square meters of surface per gram.

Numerous forms of micro-organisms may be damaging to health or an indicator of poor water quality.

For example, coliforms are common, rod-shaped bacteria that are harmless in and of themselves. Like turbidity and suspended solids, coliforms act as indicators: their presence suggests that other, more dangerous microorganisms could survive water treatment and may be present in the supply. The EPA goal for coliforms is zero trace, but the enforceable limit allows 5% of all samples within a single month to test positive. New York City tested positive for 46 of 9958 samples taken in 2010 (or 1.3% of samples in the highest month).

Also for example, *Escherichia coli* (*E. coli*) bacteria are also rod-shaped bacteria, and the majority of strains are harmless. Some strains, such as O157:H7, cause food poisoning by excreting toxic chemicals that can be life threatening for vulnerable individuals. *E. coli* is transmitted as a result of eating unwashed or undercooked food. Infectious *E. coli* can also be found in water contaminated with fecal matter, such as agricultural runoff.

As further examples, *Cryptosporidium* and Giardia are single-celled microbes often found in water systems contaminated by sewage. Much larger than bacteria, these protozoa cause digestive problems, especially in vulnerable populations.

The water treatment subsystem 206 ensures that a supply of clean, healthy water is supplied to the habitable environment 100 (Figure) for example via taps such as the faucets 130, 136 (FIG. 1) or showerhead 132 (FIG. 1). The water treatment subsystem 206 may use a multi-step approach.

The water treatment subsystem 206 may include one or more mechanical filters 259. The mechanical filters 259 may include one or more sediment or coarse filters to filter sediment or larger particulate matter from the water. The mechanical filters 259 may include one or more fine filters to filter fine particulate from the water. Various types of coarse filter and/or fine filter media may be employed, including wire mesh screens, diatomaceous earth, ceramic water filter elements.

The water treatment subsystem 206 may include one or more activated charcoal filters 260. The activated charcoal filters may remove particulate in the size range of approximately 0.5 micrometers to 50.0 micrometers.

As an alternative to adding chemical disinfectants, water can be disinfected by irradiation with UV light. The high-energy light damages the DNA of microorganisms, making it less possible for them to reproduce. UV treatment is highly effective in clear, sediment-free water. Thus, the water treatment subsystem 206 may employ Ultra-Violet Germicidal Irradiation (UVGI), in an attempt to eliminate microorganisms without using chemical-based filtering. In particular, the water treatment subsystem 206 may include one or more ultraviolet (UV) illumination sources 261 operable to expose the water to UV illumination of sufficient intensity and for sufficient time as to render pathogens in the water non-harmful. The UV illumination sources 261 may be supplied electrical power from one or more dedicated electrical power supplies 262.

As an alternative, a reverse osmosis system (not shown) preceded by a carbon filter may replace the sediment filter and ultraviolet irradiation for the removal of chlorine, PPCPS, disinfectant byproducts, heavy metals, microbes, and water hardeners.

The water treatment subsystem 206 may include one or more reservoirs of vitamin C 263 and one or more ports, valves, or manifolds 264 operable to release vitamin C into the water. The ports, valves, or manifolds 264 may be fluidly coupled to release vitamin C only in certain plumbing runs, for example supplying vitamin C only to water going to the showerhead 132 (FIG. 1) or optionally the faucet 130 associated with the tub or shower stall 122 (FIG. 1). An infusion of vitamin C into shower water may remove residual chlorine. In high concentrations, the skin can absorb vitamin C for example when applied as a topical cream. While these levels are significantly higher than those present in the showers, the shower water still provides the skin with small amounts of nutrients.

The air treatment subsystem 208 may include a variety of components to ensure that air supplied to the habitable environment 100 (FIG. 1) is healthy and comfortable for the occupant(s).

Good air quality is one of the most important features of a healthy environment. Stationary adults typically inhale 6 to 10 liters of air each minute. This amount doubles with moderate activity and doubles again with rigorous exercise. Approximately 15 cubic meters of air pass through the lungs of a moderately active adult each day.

Minute quantities of gaseous pollutants and particulates are present in the air from both natural and anthropogenic sources, which can cause serious health problems. Reducing the sources of gases and particulates in the home will decrease their negative effects. Airborne contaminants generated by materials, and the presence of individuals in the home, require expulsion through ventilation to the outdoors, and filtration to ensure that they do not return to the indoor air supply.

The major health effects of poor air quality are lung cancer and cardio-pulmonary disease. A significantly greater number of deaths from these ailments are attributable to periods of higher levels of particulate matter. Other effects of air quality are asthma attacks, emphysema, and interference with the immune system.

At the microscopic scale, natural laws concerning fluid dynamics and gravity work differently, allowing solids and liquids to float in the air almost indefinitely. Put broadly, this microscopic particulate matter is divided into two categories: fine particles, smaller than 2.5 µm ($PM_{2.5}$); and coarse particles larger than 2.5 µm and smaller than 10 µm ($PM_{10-2.5}$). Fine particles are inhalable particles that can lead to a number of health issues. Due to physical processes that govern their formation, fine particles are inherently more acidic and mutagenic than their larger counterparts. Fine particles are drawn deep into the lungs, maximizing damage. Most cases of mortality from inhalation of coarse particulate matter and larger contaminants arise from toxic chemicals they contain rather than the particles themselves.

Coarse particles do not penetrate as deeply into the lungs as fine particles, and therefore are the less dangerous of the two. However, many coarse particles are allergens. For example, dust mites are microscopic arachnids that feed on pet dander, dead human skin cells, and other biological matter. They thrive in carpets, mattresses, and curtains, and tend to dwell in synthetic fibers rather than natural materials. Mites are not inherently dangerous, but their droppings contain chemicals that trigger an immune response in some individuals. The resulting symptoms often include itchy eyes, runny nose, and wheezing, a reaction that can be particularly debilitating for asthmatics. Nearly one quarter of American homes have dust mite levels associated with symptomatic asthma, and almost half contain enough dust mites to cause allergic reactions in susceptible individuals.

The air treatment subsystem 208 may include one or more mechanical air filters (e.g., mesh, screen, woven, or piled material) 265, through which air passes to remove larger particulate. Suitable mechanical air filters may include an activated carbon air filter, high efficiency particulate (HEPA) air filter (i.e., MERV equivalent 17+), MERV 13-16 air filter, a quantity of Zeolite, or a porous material.

The air treatment subsystem 208 may include one or more electrostatic filters or precipitators 266 to remove fine particulate. In particular, electrostatic filter(s) 266 trap particles that could contain allergens, toxins, and pathogens. In addition, the electrostatic filter(s) 266 are installed to reduce dust mites, pollen, carpet fibers, mold spores, bacteria, smoke, and diesel particulate matter from the air. The electrostatic filter(s) 266 attracts particles using an electrostatic charge and extracts them from the air into a wire mesh.

The electrostatic filters 266 may take a variety of forms, for instance ones which place a charge on particles and an opposite charge on a screen or other electrode element to attract the charged particles. An example of such is a corona discharge type of electrostatic filter. The electrostatic filter 266 may be supplied charge via an electrical power supply 267.

Various airborne pathogens may present problems, particularly in enclosed spaces or habitable environments. This may be of particular concern with newer construction techniques which are employed to reduce the exchange of air with the exterior environment, for instance to reduce heat loss and thereby increase thermal efficiency. Although most airborne microbes are pervasive and generally harmless, some can be dangerous pathogens easily spread throughout a home's ventilation system.

Mold spores can induce skin, nose, throat, and eye irritation, and trigger asthma attacks. These fungi release volatile organic compounds that produce the characteristic "moldy" odor and have been linked to dizziness and nausea. Humidity control has been proven effective in reducing mold, and insulated windows reduce condensation so as to prevent mold from growing in nearby joints.

Individual microbes are very small and can evade some filters if not attached to other particles. In order to reduce the probability of airborne pathogens from traveling through the enclosed space or habitable environment 100 (FIG. 1), UVGI can be used to provide additional protection. UVGI is based on a specific frequency of UV light that specifically targets the DNA of microbes and viruses passing through the ventilation system.

The air treatment subsystem 208 may include a UV air sanitizer designed to disinfect air via UV light within one or more components (e.g., ducts) of a ventilation system. The aim is to sterilize airborne bacteria, viruses, dust mites, and mold spores that may have escaped filtration.

Thus, the air treatment subsystem 208 may include one or more UV illumination sources 268. The UV illumination source(s) 268 is positioned to illuminate air with UV illumination of a sufficient intensity for a sufficient time as to render pathogens non-harmful.

Various gaseous pollutants may produce harmful effects in humans, particularly where allowed to accumulate in habitable enclosed spaces. Volatile Organic Compounds (VOCs) are carbon-based chemicals that evaporate into gases at room temperature. Many paints, cleaning products, and pest control chemicals emit VOCs, whose presence in buildings is 2 to 5 times as high as outside levels. Some furniture and building materials also slowly release some kinds of VOC, such as formaldehyde. In the short term, exposure can cause dizziness, nausea, headaches, throat irritation, and fatigue, while chronic effects include damage to the liver, kidneys, and central nervous system.

Nitrogen dioxide is a product of combustion and mainly found near burning sources. Indoor areas that contain gas stoves, fireplaces, and cigarette smoke often have a much higher concentration of nitrogen dioxide. Epidemiological studies suggest that excessive nitrogen dioxide inhalation may decrease lung function, particularly in children. In the short term, it can also trigger allergic responses from the immune system, resulting in irritation of the eyes, nose, and throat.

Ozone is created by reactions between molecular oxygen, nitrogen oxides, and sunlight. It is the major catalyst in the formation of smog. Ozone impedes cellular respiration, resulting in reduced cell activity. High concentrations of inhaled ozone can result in an itchy throat and chest tightness; chronic exposure scars the lung tissue, which can lead to emphysema. In addition, ozone interferes with the body's immune system, which compounds the danger from air or water-borne pathogens. Under current standards, the E.P.A. expects ozone to cause more than 110,000 lost work days and 1,100,000 lost school days between 2008 and 2020.

The design of the habitable environment 100 (FIG. 1) avoids or at least reduces the use of materials which emit VOCs, for example omitting or avoiding products or materials containing certain glues or resins (e.g., particle board). In day-to-day use, materials which emit VOCs are also avoided. For instance, the care or maintenance of the habitable environment 100 (FIG. 1), avoids the use of cleaning compounds which are known to result in VOC emission.

Nevertheless, some VOCs and other gaseous pollutants may appear in the habitable environment. Thus, the air treatment subsystem 208 may include one or more activated carbon air filters 249 in the flow path to reduce VOC, nitrogen dioxide, and ozone that pass through activated carbon media filters designed to intercept gas molecules. Activated carbon air filters 249 are most useful in areas with sources of fumes or odors.

Additionally or alternatively, the electrostatic filter 266 or some other element may optionally include one or more catalysts selected to catalyze certain impurities in the air. For instance, the electrostatic filter 266 may include one or more catalysts (e.g., non-metal catalysts for instance: titanium dioxide, chromium oxide or aluminum oxide, or metal catalysts for instance: Fe, Co, Ni, Cu, Ru, Rh, Pd, Ag, Ir, Pt and Au, as well as combinations or alloys thereof, such as an alloy of Pt and Rh) to catalyze species of VOCs into more acceptable or less harmful forms.

The air treatment subsystem 208 may include one or more heaters 269 to heat air. The heaters 269 may take any of a large variety of forms. Heaters 269 may take the form of various electric heaters, which employ a resistive radiant element to heat air. Heaters 269 may take the form of forced air heaters which typically include burners that burn a fuel such as natural gas or propane. Heaters 269 may alternatively take the form of oil furnaces, or the like.

The air treatment subsystem 208 may include one or more compressors 270 which may form part of an air conditioner cooling unit. The compressors 270 may be fluidly coupled to control pressure of a fluid, coupled with one or more coils or other heat exchangers, and may operate in a similar fashion to standard air conditioner units to remove heat from the air.

Relative humidity is the measure of water vapor in the air compared to the total amount that can be held at a given temperature. In the spring and summer months, humidity levels can be high enough to cause discomfort. When cool air flows through central air systems, humidity in the air is reduced, since cooler air holds less water vapor. However, as dry air is drawn in and heated within a building in the winter, relative humidity falls, so the air feels dry.

To maintain comfort, and prevent the establishment and growth of mold, dust mites, and bacteria, relative humidity in the habitable environment 100 should be kept between 30% and 50%. Using high-temperature water within the ventilation system of the home suppresses bacteria growth. Humidity towards the bottom of this range is better in terms of air quality, but extremely low moisture levels may lead to dry skin and respiratory irritation.

Thus, the air treatment subsystem 208 may include a humidifier and/or dehumidifier 271 which controls humidity throughout the enclosed habitable environment 100 (FIG. 1). This is particularly important when moisture levels in the air fall in winter, thus the air treatment subsystem 208 must increase the moisture (i.e., humidify) during dry periods. Conversely, the air treatment subsystem 208 lowers moisture (i.e., dehumidifies) during humid periods. The humidifier and/or dehumidifier 271 may include a reservoir (not shown) that retains water to either be added to the air in a humidification mode or removed from the air in a dehumidification mode. The humidifier and/or dehumidifier 271 may include a compressor (not shown) used to, for example cool air as part of removing moisture. The humidifier and/or dehumidifier 271 may optionally include a heating element to heat air as part of adding moisture.

To control relative humidity, the air treatment subsystem 208 may additionally employ exhaust vents 158*a* (FIG. 1), particularly in the bathroom 100*b* (FIG. 1) used to increase the ventilation rate in that portion of the habitable environment in order to rapidly lower humidity generated therein, for example from showers 122, 132 (FIG. 1).

The air treatment subsystem 208 may include one or more fans and/or blowers 272 coupled to one or more ducts (FIG. 1) and/or vents (FIG. 1). The fans and/or blowers 272 may circulate air within the air treatment subsystem 208 and/or within the habitable environment 100 (FIG. 1). The fans and/or blowers 272 may expel air to an exterior environment and/or draw fresh air from the exterior environment, prior to treating the fresh air. In particular, a high flow ventilation system expels indoor air to reduce the buildup of internally generated air impurities such as volatile organic compounds, dust mites, and pet dander. A heat exchanger may advantageously be employed to recover energy from the outgoing air.

As an alternative for humidity control, a waterfall (not shown) in the enclosed space can both increase and decrease the relative humidity. When chilled water is circulated in the waterfall, the system absorbs water vapor from the air. When room temperature or warm water is circulated in the waterfall, the system releases water vapor into the air. The waterfall may also provide a soothing background sound in the habitable environment 100.

The practice of aromatherapy employs a wide variety of oils and extracts, with differing effects on mood and emotion. Supporters of contemporary aromatherapy practices suggest that various fruit and plant-based aromas have the ability to positively affect mood, behavior, and perceptions of wellness. Examples of plant-based scents and their corresponding benefits include:

Lavender effects include restful sleep during exposure at night, increased vigor the morning after nighttime exposure enhanced mood, decreased heart rate and increased positive mood. Jasmine effects include relaxation, decreased heart rate and increased positive mood. Orange scent has been used to reduce anxiety and help maintain better mood in stressful circumstances. Rosemary has been shown to enhance memory and increases reaction times.

The scent subsystem 210 is operable to selectively dispense or disperse one or more scents into the air in the habitable environment 100 (FIG. 1) or a portion thereof. The scent subsystem 210 may include a number of reservoirs 273 which hold various scents (e.g., lavender, rosemary), typically in a liquid form. One or more vents, valves or manifolds 274 are selectively operable to fluidly communicably couple selected ones of the reservoirs to emit or disperse scent into the habitable environment 100 (FIG. 1) or a portion thereof, for example via ducts or vents of the air treatment subsystem 208. The scent subsystem 210 may optionally include one or more fans and/or blowers 275 to assist in dispersing the scent(s) into the habitable environment 100 (FIG. 1) or a portion thereof. The scent subsystem 210 may optionally include one or more heaters 276, thermally (e.g., conductively, radiantly, convectively) coupled to the reservoirs 273 or an output of the reservoirs 273 to heat and thereby vaporize liquid forms of the scent(s) into a gaseous form more easily dispersible into the habitable environment 100 (FIG. 1) or a portion thereof.

Additionally or alternatively, one or more passive components may be employed to diffuse scents into the habitable environment 100. For example, various items or objects may be impregnated with specific scents. Such items or objects may include various fabrics, such as curtains, linens or bedding (e.g., pillow cases, pillows, sheets, blankets, comforters, duvets), carpets, towels, etc. Such items may include a pouch, sack or other breathable encasement or enclosure, which may be positioned at various locations about the habitable environment 100, for instance in a flow path of a vent or within a pillow case. The pouch or sack may be distributed in an air-tight packet, container or envelope which is opened immediately prior to use. Such may advantageously maintain the scent emitting materials fresh between manufacture and use, and may prevent undesired scents from being emitted into the habitable environment. Thus, certain packets may be opened to customize the scent to a specific occupant or occupants of the habitable environment 100, and the scent(s) allowed to disburse or disperse through the habitable environment 100.

Thus, active or passive components of a scent subsystem 210 deliver room-specific aromatherapy based on the room's function and aroma benefit. A wide variety of essential oils and crafted aromas are available for use in the dispenser with the option to tailor to individual specifications.

The sound subsystem 212 provides sound into the habitable environment 100 (FIG. 1) or a portion thereof. In particular, the sound system may, for example, provide soothing sounds (e.g., running water, forest sounds, waves, "white" noise, "pink" noise, music). The sound subsystem 212 may include one or more speakers 277, which may be positioned throughout the habitable environment 100 (FIG. 1) or a portion thereof. Sounds may be selected to produce relaxation or to allow an occupant to focus more intently than the occupant would focus without the sounds, for example while reading or working. The sound subsystem 212 may include one or more amplifiers 278 electrically, optically or wirelessly coupled to provide signals to the speakers 277 (e.g., typically analog or digital electrical signals) that cause the speakers 277 to reproduce the sounds represented by the signals. The sound subsystem 212 may optionally include a nontransitory computer- or processor-readable storage media 279 that stores digital versions of the sounds, for example in a library. The amplifier 278 may include one or more CODECs and/or microcontrollers to convert the digital versions of the sounds into signals for controlling the speakers 277. The sound subsystem 212 may include one or more microphones (not shown) to detect noise in the habitable space. The sound subsystem 212 may provide masking sound to offset or cancel the noise.

The input/output (I/O) subsystem 214 is communicatively coupled to the control subsystem 202 to supply input thereto and/or to provide output therefrom. The input/output (I/O) subsystem 214 may include various sensors 280-282, user operable input/output (I/O) devices, controls, panels or kiosks 283, 284, and other devices or components such as televisions 285.

For example, one or more occupant sensors or detectors 280 may be positioned in, or proximate the habitable environment 100 (FIG. 1) or portions thereof. The occupant sensor(s) or detector(s) 280 sense or detect a presence, or conversely an absence, of an occupant in the habitable environment 100 (FIG. 1). The occupant sensors or detectors 280 may take any of a large variety of forms. For example, the occupant sensor(s) or detector(s) 280 may take the form of various motion detectors, for instance passive infrared based motion detectors, proximity (RF) based motion detectors, microwave or radar based motion detectors, ultrasonic based motion detectors, vibration based motion detectors, and/or video based motion detectors. The occupant sensor(s) or detector(s) 280 may include simple contact switches which detect movement or operation of a fixture or some other element (e.g., turning on a radio, television, stereo, appliance) by an occupant. The occupant sensor(s) or detector(s) 280 may take the form of simple cameras (e.g., digital camera) which may capture images, from which changes from frame to frame may indicate a presence or absence of an occupant. The occupant sensor(s) or detector(s) 280 may detect a presence or absence of an object associated with the occupant, for instance a smartcard or keycard, or a handheld or mobile device.

Also for example, one or more temperature sensors or detectors 281 may be positioned in, or proximate the habitable environment 100 (FIG. 1) or portions thereof. The temperature sensor(s) or detector(s) 281 sense or detect a temperature proximate the temperature sensor or detector and provides signals to the control subsystem 202 and/or air treatment subsystem 208 indicative of the sensed or detected temperature. The temperature sensor(s) or detector(s) 281 may employ various components, for example thermocouples or thermally responsive resistors.

Also for example, one or more humidity sensors or detectors 282 may be positioned in, or proximate the habitable environment 100 (FIG. 1) or portions thereof. The humidity sensor(s) or detector(s) 282 sense or detect humidity or relative humidity proximate the humidity sensor or detector 282 and provides signals to the control subsystem 202 and/or air treatment subsystem 208 indicative of the sensed or detected humidity. The humidity sensor(s) or detector(s) 282 may employ various components.

One or more in-room user operable input/output (I/O) controls, panels or kiosks 283 may allow an occupant or facility personnel (e.g., cleaner, maintenance) to interact with the environmental control system 200. The in-room I/O control(s), panel(s) or kiosk(s) 283 may include a touch-sensitive or touch-responsive display, which allows presentation of information and a graphical user interface (GUI). The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs to select from, the programs. The programs may be presented in a simple fashion with simple labels or names, yet may have fairly complicated sets of settings for various combinations of the subsystems 202-214.

The in-room user operable I/O control(s), panel(s) or kiosk(s) 283 may also allow collection of information from an occupant which is indicative of the occupant's impressions and overall satisfaction with the habitable environment 100, and particularly the health and wellness amenities. Such may be captured with an automated survey, which includes various questions and possible ratings, presented for instance via a graphical user interface (GUI).

One or more facility user operable I/O controls, panels or kiosks 284 may allow facility personnel (e.g., clerk, concierge, cleaner, maintenance personnel) to interact with the environmental control system 200. The facility I/O control(s), panel(s) or kiosk(s) 284 may include a touch-sensitive or touch-responsive display, which allows presentation of information and a GUI. The information may include information about the current settings of the environmental control system 200 and different settings which may be selected by the user. The GUI will include one or more user selectable icons (e.g., scroll bars, tool bars, pull down menus, dialog boxes, keys, text) displayed for selection by the user. Selection may allow the user to adjust illumination, temperature, humidity, sound, or other aspects of the environment. The GUI may present the user with a set of defined programs to select from, the programs. The programs may be presented in a simple fashion with simple labels or names, yet may have fairly complicated sets of settings for various combinations of the subsystems 202-214. The GUI may optionally allow facility personnel to define new programs, delete old programs, and/or modify existing programs.

The GUI may, for example, allow facility personnel to enter information about a specific guest or other occupant that will occupy a respective habitable environment. Information may, for example, include a location from which the occupant originated. The location may be specified in a variety of forms including name (e.g., city, state, country), geographic coordinates (e.g., latitude and/or longitude). Such may allow the environmental control system 200 to determine a control program that accommodates for changes experienced by the occupant due to travel to a new location. Thus, the environmental control system 200 may adjust for changes in the diurnal cycle and/or circadian cycle. Information may include an age or approximate age of the occupant, which may affect or be related to circadian cycle and the ability to adjust for travel (e.g., "jet lag"). Such may allow accommodation or treatment for other issues, for instance seasonal affective disorder, or providing light therapy to treat certain aliments or symptoms.

As noted previously, one or more televisions 285 may be used to at least present information to an occupant. In some implementations, a control such as a remote control, may be used by the occupant to interact with the television 285 to make selection of various user selectable options for controlling one or more components of the environmental control system 200. As also previously noted, an occupant may use a handheld or mobile device 182c (FIG. 1), such as a smart phone, tablet computer, etc. to interact with environmental control system 200.

The server 244 and nontransitory computer- or processor-readable medium 246 may store and provide information to other components of the environmental control system 200. Such may, for instance, include a schedule that specifies which occupants will occupy which habitable environments 100 (FIG. 1) of the facility, and at what times. This information may also specify, or be mapped to, information which specifies desired environmental characteristics for the respective occupants. Thus, the environmental control system 200 may automatically adjust environmental characteristics in a variety of habitable environments 100, customized for the particular occupant.

A sanitizing subsystem 216 may be an integral part of the habitable environment 100, or may be selectively provided thereto or therein, for example when preparing for another occupant or guest. For instance, the sanitizing subsystem 216 may be provided as a cart with wheels, as illustrated in FIG. 2, for selectively being wheeled into the habitable environment 100. While illustrated as a cart, the sanitizing subsystem 216 may be provided as a portable unit which may be hung from a pole mounted approximately centrally in the habitable environment, or wall or less preferably hung from a wall or other structure in the habitable environment 100. Such may advantageously allow the sanitizing subsystem 216 or a portion thereof to be positioned at a higher point than might otherwise be achieved via a cart.

The sanitizing subsystem 216 may provide a sanitizing agent into the habitable environment 100 to destroy or render non-harmful various pests or pathogens. The sanitizing subsystem 216 may optionally evacuate the sanitizing agent from the habitable environment 100 (FIG. 1), after a sufficient time has passed for the sanitizing agent to destroy or render non-harmful the pests or pathogens.

The sanitizing agent may take a variety of forms. The sanitizing agent may be in a gaseous form, or may be a vapor or "dry vapor" (i.e., non-wetting) form. Suitable sanitizing agents may, for example, include forms of chlorine dioxide, peracetic acid, hydrogen peroxide and electrochemically activated solutions (e.g., electrolyzed water). Suitable sanitizing agents may, for example, include photocatalytic antimicrobial materials (e.g., composite photocatalyst, nanoparticle sized zinc metal in a matrix of nano-crystalline titanium dioxide available under the trademark OXITITAN™ from EcoActive Surfaces, Inc. of Pompano Beach, Fla.). Such may provide an antimicrobial surface, reduce odor and VOCs, provide for hydrophilic or hydrophobic self-cleaning, and/or UV or corrosion protection. The UV protection may be particularly advantageous where UV illumination is also utilized in sanitizing the habitable environment 100.

Alternatively, or additionally, the sanitizing agent may be in the form of electromagnetic energy or radiation, for example specific ranges of wavelengths such as UV of electromagnetic energy.

A sanitizing subsystem 216 may include one or more reservoirs of sanitizing agent(s) or materials 286 which when combined produce a sanitizing agent. The sanitizing subsystem 216 may include one or more fans or blowers 287 to assist in dispersing the sanitizing agent into the habitable environment 100 (FIG. 1). In some implementations, the fan(s) or blower(s) 287 also assist in removing or evacuating the sanitizing agent into the habitable environment 100 (FIG. 1). The sanitizing subsystem 216 may optionally include one or more transducers 288 operable to place the sanitizing agent in a form more amenable to dispersion. The transducer(s) 288 may take the form of a heater, for example to vaporize the sanitizing agent. Additionally or alternatively, the transducer(s) 288 may take the form of one or more high frequency vibration elements (e.g., piezoelectric element) to pulverize or otherwise particalize either dry sanitizing agent into a very fine particulate form or to break up droplets of liquid sanitizing agent into a very fine form, for instance that does not wet surfaces. Other types of transducers 288 may be employed.

The sanitizing subsystem 216 may include one or more ports or vents 289 for dispersing the sanitizing agent. Ports or vents 289 may be built into a housing 290 of the sanitizing subsystem 216. Additionally, or alternatively, the sanitizing subsystem 216 may include one or more hoses 291 with nozzles 292 or other openings for dispersing the sanitizing agent.

The sanitizing subsystem 216 may include one or more wands selectively operable to emit electromagnetic energy or radiation, for example specific ranges of wavelengths such as UV of electromagnetic energy. The wand(s) may include one or more illumination sources, for instance UV illumination sources and may be electrically coupled to a power source 297 carried by the cart via one or more cables 298. Alternatively, illumination sources may be located in the cart, and the wand(s) optically coupled thereto via one or more cables 298.

The sanitizing subsystem 216 may include one or more illumination sources positioned so as to be exposed to the ambient environment in order to provide illumination into the habitable environment 100 directly from a housing of the sanitizing subsystem 216. The illumination sources positioned on an exterior of the cart or within the exterior of the cart and optically communicatively coupled to the exterior via one or more optical ports (not shown). This may allow the general habitable environment 100 to be optically treated, for instance with UV illumination. The wand(s) may, for instance, be used to treat areas or spaces that would not otherwise be treated via direct illumination from the illumination sources, for instance areas or spaces that are not in a direct line of sight of the illumination sources. In some implementations, the illumination sources may provide the illumination which is optically coupled to the wand(s) via the cable 298.

Sanitizing may require as little as three hours of exposure to UV illumination, dependent of a variety of factors such as type of pathogens, distance, and intensity (e.g., incident energies). Targeted pathogens may take a variety of forms, for example mold spores, and organisms such as various *bacillus*, protozoa, virus, yeast. Mold spores may include, for instance: *Aspergillius flavis, Aspergillius glaucus, Aspergillius niger, Mucor racemosus* A, *Mucor racemosus* B, *Oospora lactis, Penicillium expansum, Penicillium roqueforti, Penicillium digitatum, Rhisopus nigricans*. Illumination may occur before, after, during, or before and after application of a photocatalytic antimicrobial agent or coating. Operation may require that the habitable space be vacant during the entire period of treatment. Thus a remote control (e.g., wireless handheld transmitter and wireless receiver in the cart 203) or a delay start timer may be advantageously employed.

Data, Data Structures, and Nontransitory Storage Media

Various nontransitory media discussed above may store information such as data including configuration information in one or more data structures. Data structures may take a variety of forms, for example records associated with relational databases, a database itself, lookup tables, etc. The data structures may store a variety of different information or data.

Operation

Figure 3:
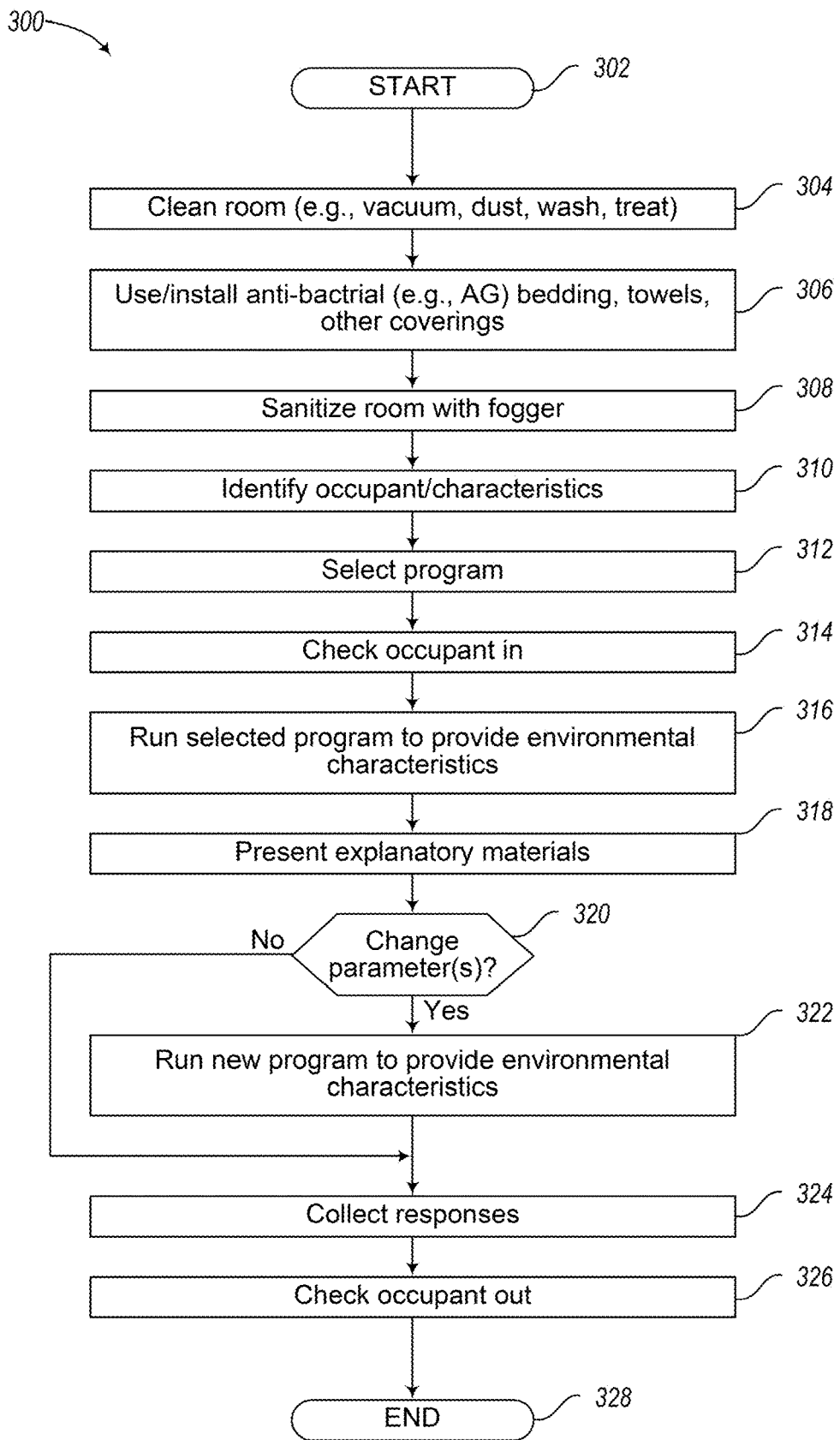
FIG. 3 is a flow diagram that shows a high level method of providing an enhanced environment in a habitable environment, according to one illustrated embodiment.

FIG. 3 shows a high level method 300 of providing an enhanced environment in a habitable environment 100, according to one illustrated embodiment. While often discussed in terms of a hotel, motel, spa or other hospitality environment, the habitable environment 100 may take the form of a home, office, hospital or any other inhabitable environment.

The method 300 starts at 302. The method 300 may, for example start on a periodic basis, for instance daily, weekly, or monthly. Alternatively, or additionally, the method 300 may start on demand, for instance in response to a checking in of a guest, or expected check in of a guest, or an entry of a guest or occupant into the habitable environment 100 (FIG. 1), for instance in response to reading an identifier from a smartcard or cardkey 114.

At 304, cleaning personnel clean the habitable environment 100. Such may include emptying waste receptacles, dusting, washing, vacuuming, cleaning and/or treating surfaces with disinfectants, and/or collecting soiled or used laundry (e.g., towels).

At 306, cleaning personnel use or install anti-bacterial bedding, towels, other coverings (e.g., drapes) in the habitable environment 100. The anti-bacterial bedding, towels, other coverings may for example be impregnated or coated with one or more anti-bacterial or anti-pathogen agents.

At 308, cleaning personnel optionally sanitize the habitable environment 100 or a portion thereof, for instance with a sanitizing subsystem 216. As previously explained, the sanitizing subsystem 216 may take a variety of forms, at least one of which is a fogger or "dry fogger" which disperses a fog or "dry fog" of a sanitizing agent into the habitable environment 100 (FIG. 1). The sanitizing agent may deposit on various surfaces, and may be left in place sufficiently long to neutralize or render pathogens or other undesirable substance harmless. As previously noted, the sanitizing agent may not "wet" the surfaces, thereby protecting the surfaces from damage. The sanitizing system 216 may then, optionally evacuate or otherwise remove the sanitizing agent from the habitable environment 100, for instance collecting such in a reservoir for disposal or recycling.

Optionally at 310, the environmental control system 200 or a portion thereof identifies one or more occupants or guests that will inhabit the habitable environment 100 (FIG. 1) and/or specific attributes, traits or characteristics of the occupant(s). For example, facility personnel may enter an occupant identifier via an input device, panel or kiosk 284. Also for example, the occupant(s) or guest(s) may enter an occupant identifier via an input device, panel or kiosk 283. As a further example, an occupant identifier may be automatically read from some piece of media, for instance a smartcard or keycard. The occupant identifier may, for example, be encoded in a magnetic stripe, machine-readable symbol, or wireless transponder (e.g., RFID transponder) of the smartcard or keycard. The occupant identifier may consist of or include the occupant's name, however preferable is an alphanumeric string which does not include the occupant's actual name. The alphanumeric string may be logically associated with the occupant's name, for example in a secure database or other secure data structure. Such an approach may enhance security.

The specific attributes, traits or characteristics of the occupant(s) may likewise be stored in a secured database or other secure data structure, or less preferably could be stored in the smartcard or cardkey. The specific attributes, traits or characteristics of the occupant(s) may specify information that allows customization of the habitable environment to the needs or desires of the occupant. For example, the specific attributes, traits or characteristics of the occupant(s) may identify one or more air temperatures, for example air or room temperatures for different times throughout a daily cycle. Also for example, the specific attributes, traits or characteristics of the occupant(s) may identify one or more air relative humidities, for example relative humidity for different times throughout a daily cycle. As another example, the specific attributes, traits or characteristics of the occupant(s) may identify one or more locations from which the occupant has traveled. Such may permit adjustment of, for example lighting, to accommodate for jet lag, SAD, etc. As a further example, the specific attributes, traits or characteristics of the occupant(s) may identify one or more syndromes, ailments or conditions for which environmental characteristics may be adjusted to alleviate or treat. These may include syndromes, ailments or conditions which may be addressed by delivery of illumination (e.g., timed delivery of different intensities and/or wavelengths). This may also include syndromes, ailments or conditions which may be addressed by delivery of humidity, for instance various skin disorders or problems. These syndromes, ailments or conditions may be specified by name or an assigned identifier. Alternatively or additionally, specific instructions or patterns may be stored for providing the desired environmental characteristics. Such may help maintain privacy for individuals, and may address regulatory issues (e.g., HIPAA) related to the care, handling and management of health-related information such as electronic medical records. Thus, for example, a pattern of illumination which specifies wavelengths and intensities at various times throughout the solar day may be stored. Patterns specifying air temperature, relative humidity, sound, scents, and other ambient environmental characteristics may likewise be stored for various times throughout the solar day. These patterns may be synchronized with one another. Thus, for example, illumination and sound may be synchronized to produce a gradual wakeup period in which light gradually increases in intensity as does soothing sounds. The wavelengths of light may likewise gradually change during this wake up period. Also for example, illumination and sound may be synchronized to produce a gradual relaxation period prior to a sleep time in which light gradually decreases in intensity as does soothing sounds. The wavelengths of light may likewise gradually change during this relaxation up period.

Optionally at 312, facility personnel, the occupant, or the environmental control system 200 or a portion thereof selects a program to execute to provide the environmental characteristics, attributes or amenities. Such may be done, for example, where no program has previously been specified or identified. Alternatively, such may be done where multiple programs are specified for a given occupant. As previously noted, the one or more programs may be stored for each perspective occupant, for example stored in a smartcard or keycard 114 or stored in a database in a nontransitory computer- or processor-readable media 246. These programs or identifiers representing these programs may be presented to the facility personnel or occupant to select from, for instance via one or more of an input device, panel or kiosk 283, 284. Alternatively, or additionally, the control subsystem 202 (FIG. 2) may select a program, for example based on certain criteria about the occupant. For instance, the control subsystem 202 (FIG. 2) may determine that the occupant has recently traveled from a location with a significantly different natural light cycle from that of the location of the habitable environment 100 (FIG. 1). Thus, the control subsystem 202 (FIG. 1) may select a program which provides specific illumination or other characteristics that alleviates or otherwise addresses symptoms or ailments associated with such changes in natural illumination due to travel, such as jet lag or SAD.

A set of patterns may be defined which accommodate changes in total amount of natural light and/or the spectral components (e.g., wavelengths) of the natural light for a large number of pairs of origination and arrival locations, where the origination location is a location from which the occupant departs (e.g., typically the occupant's home) and the arrival location is a location to which the occupant has traveled (e.g., a hotel, motel, spa). These patterns may, for example, relate each of 24 time zones (e.g., zones of longitudes) to the other 23 time zones throughout the World. These patterns may relate to various latitudes or zones of latitudes throughout the World. For instance, patterns may be established for each pair of latitude zones (e.g., 5 degree increments of latitude) north and south of the equator. Thus, each latitude zone may be related to each other latitude zone by a respective pattern. Patterns may likewise be defined for various pairs of geographical locations (e.g., longitude or time zone, and latitude) to simultaneously accommodate for both time zone changes and changes in length of solar day. Patterns do not have to be established for all possible pairs of geographic locations since most occupants will arrive from a relatively small number of geographic locations, and since the geographic location of the arrival location is presumably known for any given inhabitable environment 100 (FIG. 1). Likewise, grouping longitudes by, for instance time zone, and/or latitudes into bands (e.g., 5 degrees) will also limit the total number of stored patterns. While described as being stored, in some implementations, patterns may be generated dynamically or "on the fly" via one or more algorithms or equations using geographic locations as input.

Optionally at 314, facility personnel may check in or register one or more occupants, for use of the habitable environment 100 (FIG. 1), in a similar or identical manner as that performed at most hotels, motels, spas or hospitals. The identification of the occupant or guest at 310 and/or the selection of the program at 312 may be performed as part of this check or registration. Alternatively, identification of the occupant or guest at 310 and/or the selection of the program at 312 may be performed prior to this check in or registration 314, for example as part of booking or reserving the habitable environment 100 (FIG. 1) as an accommodation.

At 316, the control subsystem 202 (FIG. 2) runs the selected program to cause the various subsystems 202-214 to provide the environmental characteristics or amenities in the habitable environment 100 (FIG. 1).

Optionally at 318, the control subsystem 202 or a portion of the environmental control system 200 present explanatory materials which explain the operation and benefits of the habitable space including the various active and passive components. Such may include presentation of a tutorial, for instance in a video form, explaining how a user may operate or otherwise interact with the environmental control system 200.

At 320, from time-to-time the control subsystem 202 or a portion of the environmental control system 200 determines whether a change has been made to any of the operational parameters. Changes may, for example, be made by occupant(s) and/or facility personnel, or via sensed or detected conditions in the habitable environment 100 (FIG. 1). For example, the occupant(s) or facility personnel may change a setting for air temperature, relative humidity, illumination, scent dispersal, or other parameter. The change(s) may be temporary or one time changes, or may be more permanent changes that will be stored for use on another occasion or for use with another habitable environment 100 (FIG. 1). Thus, the control subsystem 202 or a portion of the environmental control system 200 may generate a new program, or execute an existing program with new or modified parameters, hence in effect constituting a new program.

If a change has been made, at 322 the control subsystem 202 or a portion of the environmental control system 200 runs the new program or program with new parameters to provide environmental characteristics. Execution of the new program causes the various subsystems 202-214 to provide the environmental characteristics or amenities in the habitable environment 100 (FIG. 1) in accordance with the new parameters.

Optionally at 324, the control subsystem 202 or a portion of the environmental control system 200 collects responses from the occupant(s) with respect to the habitable environment 100 (FIG. 1). In particular, the control subsystem 202 or a portion of the environmental control system 200 may provide an opinion survey and/or questions regarding the occupant(s) objective and/or subjective impressions of the effect of the accommodations on their overall health and/or wellness or sense of wellness. Such may also inquire regarding actual operation of the environmental control system 200, as well as the ease of use or interaction with the same. The survey or questions may provide a scale for rating the occupant's experience, and in particular sense of wellbeing.

Optionally at 326, facility personnel check out the occupant or guest. The facility personnel preferably actively inquire about the occupant's or guest's sense of wellbeing and experience with the amenities of the habitable environment 100 (FIG. 1). At this time, the facility personnel may update patterns, store new patterns, and/or delete old patterns associated with the particular occupant or guest, providing a refined experience on the occupant's next visit or use of the habitable environment 100 (FIG. 1) or other inhabitable environment 100 (FIG. 1) for instance at another location.

The high level method 300 may terminate at 328 until started again, or may continually repeat. Alternatively, the high level method 300 may run concurrently with other methods or processes.

Figure 4:
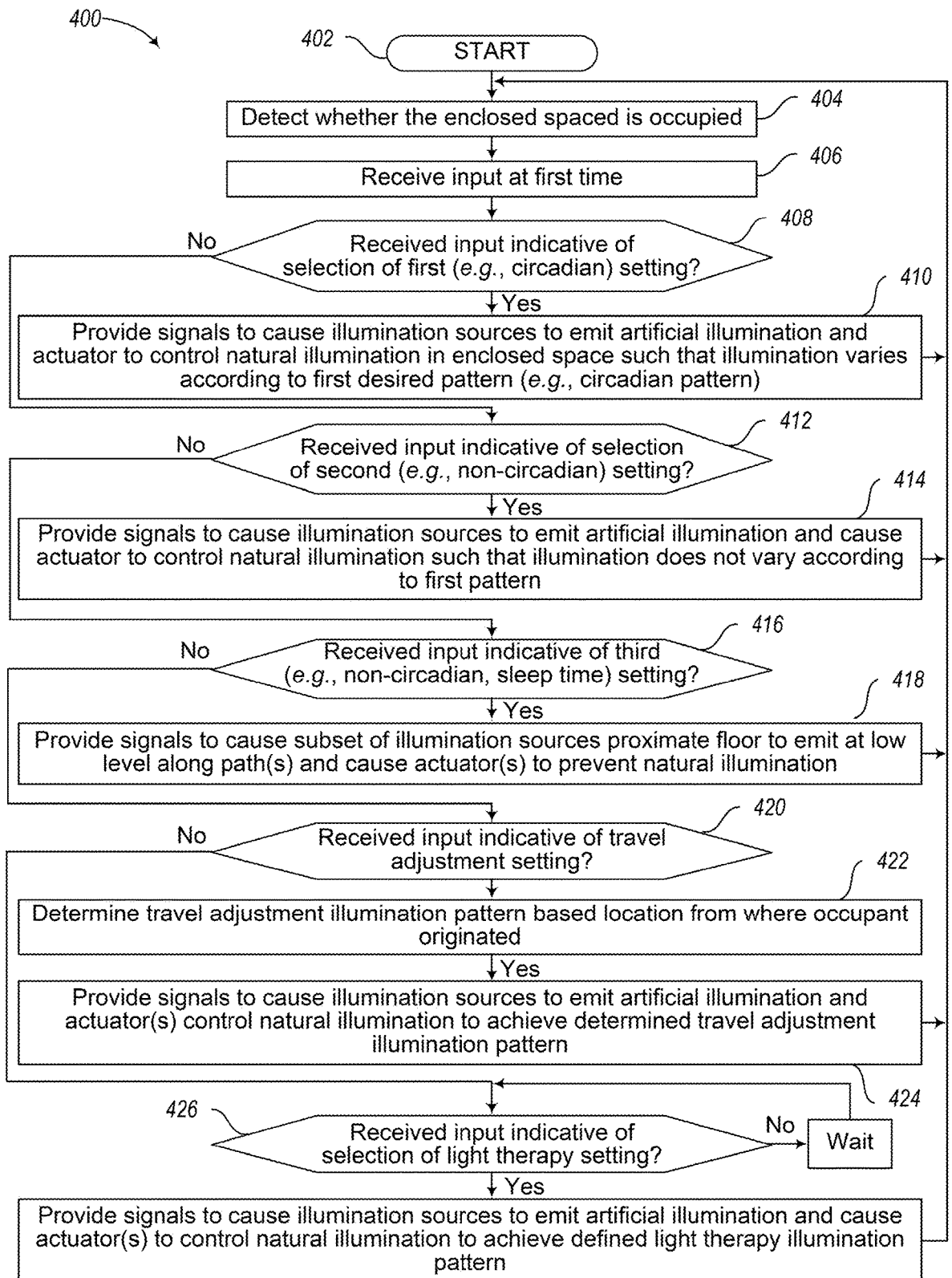
FIG. 4 is a flow diagram that shows a low level method of operating one or more components of a habitable environment enhancement system for providing illumination, according to one illustrated embodiment, which may be useful in performing at least a portion of the method illustrated in FIG. 3.

FIG. 4 shows a low level method 400 of operating one or more components of a habitable environment enhancement system for providing illumination, according to one illustrated embodiment, which may be useful in performing at least a portion of the method 300 illustrated in FIG. 3.

The low level method 400 starts at 402. The method 400 may, for example run continuously, or may start on a periodic basis, for instance every few minutes, hourly, daily, weekly, monthly. Alternatively, or additionally, the method 400, or portions thereof, may start on demand, for instance in response to detection of an occupant of the habitable environment 100, or in response to a request by a guest or operator of a facility (e.g., hotel, spa, resort, hospital).

Optionally at 404, a sensor or detector senses or detects whether the enclosed spaced is occupied. The sensor(s) may, for example, provide signals to the control subsystem indicative of whether the enclosed space is occupied. One or more of the following acts may be selectively performed based on the signals. For example, it may be more energy efficient to avoid providing active illumination when the habitable environment is not occupied.

At 406, a control subsystem receives an input, for example at a first time. The input may be indicative of any of a number of settings, for instance settings related to illumination to be provided in an enclosed space. The input may be received via at least one user actuatable input device located within the enclosed space or at an entrance to the enclosed space. Additionally or alternatively, input may be received via at least one user actuatable input device located remotely from the enclosed space. For example, located at a reception, concierge, building maintenance or other centralized location associated with the building.

At 408, the control subsystem determines whether the received input is indicative of a selection of a first setting. The first setting may, for example, be a circadian setting, that is a setting or pattern of illumination that is consistent with and establishes a natural circadian rhythm or cycle in a human. Such may, for example, mimic the intensity and chromatic makeup of natural sunlight and darkness over a solar day at some given location on the Earth.

At 410, in response to determining the first input indicates a first setting, the control subsystem provide signals to cause at least some of the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination varies over a first period of time according to a first pattern. The first pattern may, for example be a circadian pattern (e.g., pattern consistent with and which establishes a natural circadian rhythm or cycle in a human).

At 412, the control subsystem determines whether the received input is indicative of a selection of a second setting. The second setting may be a first non-circadian setting, that is any setting or pattern of illumination other than a setting or pattern of illumination that is consistent with and establishes a natural circadian rhythm or cycle in a human.

At 414, in response to the second input the control subsystem provides signals to cause the illumination sources to emit artificial illumination at a number of levels and a number of wavelengths and to cause at least one actuator to control at least a level of natural illumination received into the enclosed space via one or more windows from an external source of illumination such that a combination of the artificial and the natural illumination does not vary over a second period of time according to a non-circadian pattern (e.g., any pattern other than a pattern consistent with and which establishes a natural circadian rhythm or cycle in a human). For example, in response to the second input, the control subsystem may provide signals to the illumination sources and the actuator(s) such that the combination of the artificial and the natural illumination remains constant over the second period of time.

At 416, the control subsystem determines whether the received input is indicative of a selection of a second non-circadian setting that is a sleep time setting at a third time.

At 418, in response to the third input the control subsystem provides signals to cause a subset of the illumination sources proximate to a floor in the enclosed space to emit artificial illumination at a low illumination level along at least one path. The signals may further cause the at least one actuator to prevent natural illumination from being received into the enclosed space via the one or more windows.

At 420, the control subsystem determines whether the received input is indicative of a selection of a travel adjustment setting.

At 422, in response to the fourth input the control subsystem determines a travel adjustment illumination pattern based at least in part on a geographic location from where an occupant of the enclosed space originated to accommodate a change in circadian rhythm due to travel by the occupant. At 424, also in response to the fourth input, the control subsystem provides signals to cause the illumination sources to emit artificial illumination at the levels and the wavelengths and to cause the at least one actuator to control at least the level of natural illumination received into the enclosed space via the one or more windows such that the combination of the artificial and the natural illumination achieves the determined travel adjustment illumination pattern in the enclosed space.

At 426, the control subsystem determines whether the received input is indicative of a selection of a light therapy setting at a fourth time.

At 428, in response to the fourth input indicative of the light setting, providing signals by the control subsystem to cause the illumination sources to emit artificial illumination at the levels and the wavelengths and to cause the at least one actuator to control at least the level of natural illumination received into the enclosed space via the one or more windows such that the combination of the artificial and the natural illumination achieves the defined light therapy illumination pattern in the enclosed space over a therapeutic period of time.

The method 400 may repeat as indicated by arrow 430. Alternatively, the method 400 may terminate until called again or otherwise restarted.

FIG. 5 shows a low level method 500 of operating one or more components of a habitable environment enhancement system to adjust an amount of natural light received in the habitable environment using electrochromatic panes, according to one illustrated embodiment, which may be useful in performing at least a portion of the method 400 illustrated in FIG. 4.

At 502, a control subsystem provides signals to control an actuator (e.g., voltage or current supply) drivingly coupled to the electrochromatic panes to adjust illumination passed thereby. For example, the signals may cause the drape(s)/shade(s)/curtain(s) (collectively window coverings) to move to a fully closed position which completely or substantially blocks natural light from entering the habitable environment 100 or portion thereof via the window(s). Alternatively, the signals may cause the drape(s)/shade(s)/curtain(s) to move to a fully open position which allows a maximum amount of natural light to enter the habitable environment 100 or a portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or a portion thereof via the window(s).

Since the intensity of natural light in the ambient environment varies throughout the day, and from day to day, control may be based at least in part to one information from one or more light sensors or detectors. The light sensors or detectors may sensor or detect natural light in the exterior ambient environment and provide the control subsystem with signals indicative of an intensity or spectral power distribution thereof. Additionally or alternatively, the light sensors or detectors may sensor or detect light in the habitable environment 100 or a portion thereof and provide the control subsystem with signals indicative of an intensity thereof.

FIG. 6 shows a low level method 600 of operating one or more components of a habitable environment enhancement system to adjust an amount of natural light received in the habitable environment using drapes or shades or curtains or other window coverings, according to one illustrated embodiment, which may be useful in performing at least a portion of the method 400 illustrated in FIG. 4.

At 602, a control subsystem provides signals to control an actuator (e.g., electrical motor, solenoid) drivingly coupled via a transmission to move drape(s)/shade(s)/curtain(s) relative to a window. For example, the signals may cause the drape(s)/shade(s)/curtain(s) to move to a fully closed position which completely or substantially blocks natural light from entering the habitable environment 100 or a portion thereof via the window(s). Alternatively, the signals may cause the drape(s)/shade(s)/curtain(s) to move to a fully open position which allows a maximum amount of natural light to enter the habitable environment 100 or a portion thereof via the window(s). The signals may cause the drape(s)/shade(s)/curtain(s) to move to a variety of intermediate positions between the fully closed and fully open positions, which intermediate positions allow respective amounts of natural light to enter the habitable environment 100 or a portion thereof via the window(s).

Since the intensity of natural light in the ambient environment varies throughout the day, and from day to day, control may be based at least in part on one information from one or more light sensors or detectors. The light sensors or detectors may sensor or detect natural light in the exterior ambient environment and provide the control subsystem with signals indicative of an intensity thereof. Additionally or alternatively, the light sensors or detectors may sensor or detect light in the habitable environment 100 or a portion thereof and provide the control subsystem with signals indicative of an intensity thereof.

Figure 7:
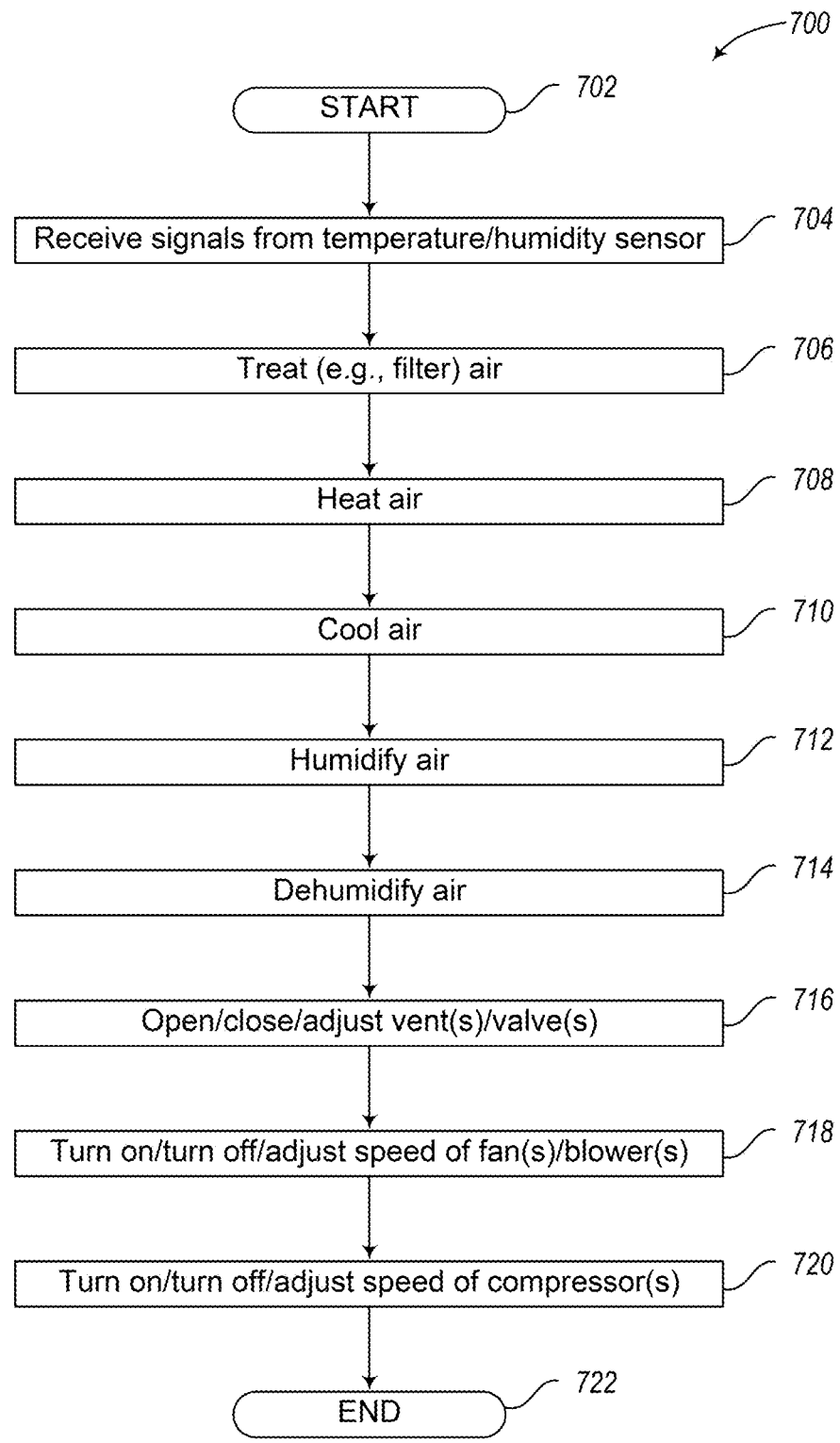
FIG. 7 is a flow diagram that shows a low level method of operating one or more components of a habitable environment enhancement system for providing heating, ventilation and cooling of a habitable environment, according to one illustrated embodiment, which may be useful in performing at least a portion of the method illustrated in FIG. 3.

FIG. 7 shows a low level method 700 of operating one or more components of a habitable environment enhancement system for providing heating, ventilation and cooling of a habitable environment 100, according to one illustrated embodiment, which may be useful in performing at least a portion of the method 300 illustrated in FIG. 3. Typically only a few of the acts identified in method 700 will be performed in any single pass. For example, cooling of air is unlikely to be performed if the air has just been heated, or dehumidifying is unlikely to be performed in humidification was just performed. Thus, method 700 provides more of a comprehensive illustration of the acts that may be performed.

The low level method 700 starts at 702. The method 700 may, for example run continuously, or may start on a periodic basis, for instance every few minutes, hourly, or daily. Alternatively, or additionally, the method 700 may start on demand, for instance in response to an adjustment of a thermostat, entry into a user input device, or sensed or detected presence of an occupant in the habitable environment 100 or a portion thereof.

At 704, the control subsystem receives signals from at least one of a temperature or humidity sensor or detector which signals are indicative of a sensed or detected temperature and/or humidity in habitable environment 100 or a portion thereof. The signals may be used in order to adjust at least one of a temperature and/or humidity of the air in the habitable environment 100, for example based at least in part on a circadian pattern over a period of time.

At 706, the control subsystem provides signals that cause air to be treated. The signals may, for example, turn ON, turn OFF, and/or adjust a speed of one or more fans or blowers. The signals may additionally or alternatively, adjust a position of a vent, damper, valve or manifold. Such may circulate or otherwise cause air to be treated by filtering via one or more mechanical (HEPA) air filters. Such may circulate or otherwise cause air to be treated by filtering via one or more electrostatic particle air filters, a voltage being supplied according to the signals. Such may circulate or otherwise cause air to be treated by exposure to ultraviolet illumination via an air ultraviolet sanitizer.

At 708, the control subsystem provides control signals which cause air to be heated. For example, the control subsystem may provide signals to a heater (e.g., forced air furnace, steam radiator) to heat air. Also for example, the control subsystem may provide signals to open, close or adjust an opening of a vent, damper, valve or manifold which routes warm air to the habitable environment 100 or a portion thereof.

At 710, the control subsystem provides control signals which cause air to be cooled. For example, the control subsystem may provide signals to a cooler (e.g., air condition, swamp cooler) to cool (i.e., remove heat from) the air. Also for example, the control subsystem may provide signals to open, close or adjust an opening of a vent, damper, valve or manifold which routes cool air to the habitable environment 100 or a portion thereof.

At 712, the control subsystem provides control signals which cause air to be humidified. For example, the control subsystem may provide signals to a humidifier to humidify (i.e., add moisture) to the air. Also for example, the control subsystem may provide signals to open, close or adjust an opening of a vent, damper, valve or manifold which routes humidified air to the habitable environment 100 or a portion thereof.

At 714, the control subsystem provides control signals which cause air to be dehumidified. For example, the control subsystem may provide signals to a dehumidifier to dehumidify (i.e., remove moisture) from the air. Also for example, the control subsystem may provide signals to open, close or adjust an opening of a vent, damper, valve or manifold which routes dehumidified air to the habitable environment 100 or a portion thereof.

At 716, the control subsystem opens, closes, or otherwise adjusts one or more vents or dampers or valves or manifolds. Operation of various vents, dampers, valves or manifolds may provide fresh air, conditioned air, and/or scents or aromas to the habitable environment 100 or a portion thereof. The vents or dampers or valves or manifolds may be operated via one or more actuators, for example electric motors or solenoids, or shape memory alloy actuators, spring loaded actuators and/or magnetic actuators.

At 718, the control subsystem provides control signals which cause air to be moved or circulated. For example, the control subsystem may provide signals to one or more fans or blowers to move or circulate the air. The signals may turn ON, turn OFF and/or adjust a speed of a fan or blower.

At 720, the control subsystem provides control signals which cause air to be compressed. For example, the control subsystem may provide signals to one or more compressors to compress air, for instance to remove moisture or as part of removing heat. The signals may turn ON, turn OFF, or otherwise adjust a speed of a compressor.

The low level method 700 may terminate at 722 until called again, or may continually repeat. Alternatively, the low level method 700 may run concurrently with other methods or processes, for example, as one of multiple threads on a multi-threaded processor system.

Figure 8:
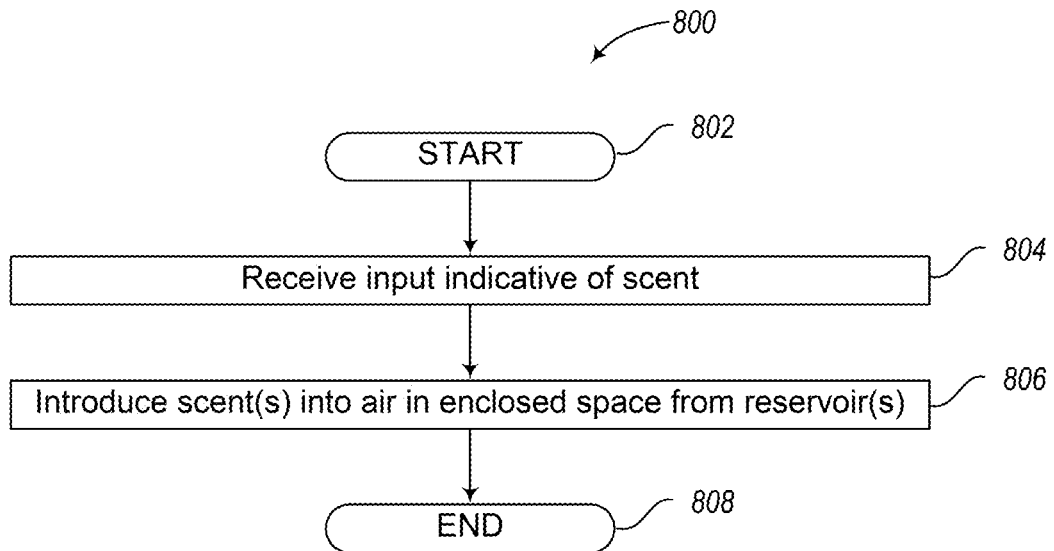
FIG. 8 is a flow diagram that shows a low level method of operating one or more components of a habitable environment enhancement system for introducing scents or aromas into a habitable environment, according to one illustrated embodiment, which may be useful in performing at least a portion of the method illustrated in FIG. 3.

FIG. 8 shows a low level method 800 of operating one or more components of a habitable environment enhancement system for introducing scents or aromas into a habitable environment, according to one illustrated embodiment, which may be useful in performing at least a portion of the method 300 illustrated in FIG. 3.

The low level method 800 starts at 802. The method 800 may, for example start on a periodic basis, for instance every few minutes, hourly, or daily. Alternatively, or additionally, the method 800 may start on demand, for instance in response to a request by a guest or operator of a facility (e.g., hotel, spa).

At 804, the control subsystem receives input indicative of a scent to be dispersed in the habitable environment 100 or a portion thereof. The input may come from an in room control panel, a remote control panel, a handheld device (e.g., smart phone, tablet computer, or personal digital assistant), or may be generated as part of execution of a program by a control subsystem.

At 806, the control subsystem provides signals which cause one or more scents to be introduced into air in the habitable environment 100 or a portion thereof. The scent(s) may be delivered from one or more reservoirs. The signals may cause a vent, damper, valve, or manifold to open, or alternatively close, allow scent to enter the habitable environment 100 or a portion thereof. The signals may additionally or alternatively cause one or more fans or blowers to cause the scent(s) to be delivered in the habitable environment 100 or a portion thereof or dispersed or circulated therein. Additionally or alternatively, the signals may cause a heater to heat scented material, for instance to vaporize the material to cause the scent to be dispersed into air which is circulated into the habitable environment 100 or a portion thereof.

The control subsystem may provide the signals to cause the scent(s) to be introduced according to or based on a defined schedule. Alternatively or additionally, the control subsystem may provide the signals to cause the scent(s) to be introduced on demand, for example in response to a user input.

The low level method 800 may terminate at 808 until called again, or may continually repeat. Alternatively, the low level method 800 may run concurrently with other methods or processes, for example, as one of multiple threads on a multi-threaded processor system.

Figure 9:
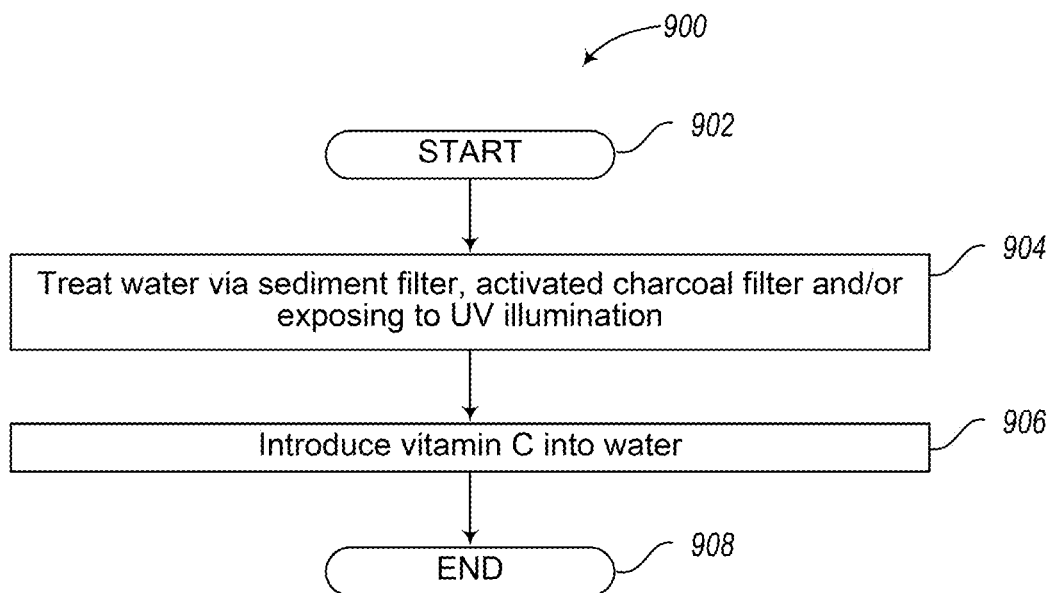
FIG. 9 is a flow diagram that shows a low level method of operating one or more components of a habitable environment enhancement system for treating water for use in a habitable environment, according to one illustrated embodiment, which may be useful in performing at least a portion of the method illustrated in FIG. 3.

FIG. 9 shows a low level method 900 of operating one or more components of a habitable environment enhancement system for treating water for use in a habitable environment, according to one illustrated embodiment, which may be useful in performing at least a portion of the method 300 illustrated in FIG. 3.

The low level method 900 starts at 902. The method 900 may, for example run continuously, or may start on a periodic basis, for instance every few minutes, hourly, or daily. Alternatively, or additionally, the method 900 may start on demand, for instance in response to use of water by an occupant of the habitable environment 100.

At 904, one or more water treatment components of a water supply subsystem treat a supply of water to a faucet or a showerhead of the habitable environment 100. Treating water may, for example include filtering water using one or more sediment or coarse particle filters. Treating water may additionally or alternatively include fine filtering of water, for example, using one or more activated charcoal filters. Treating water may additionally or alternatively include exposing the water to ultraviolet illumination of sufficient intensity and duration as to sanitize the water.

At 906, one or more water treatment components of the water supply subsystem introduce vitamin C into at least some of the water. For example, one or more valves or manifold may release vitamin C from a reservoir of vitamin C into water that is to be supplied to the showerhead of the habitable environment 100.

The low level method 900 may terminate at 908 until called again, or may continually repeat. Alternatively, the low level method 900 may run concurrently with other methods or processes, for example, as one of multiple threads on a multi-threaded processor system.

Figure 10:
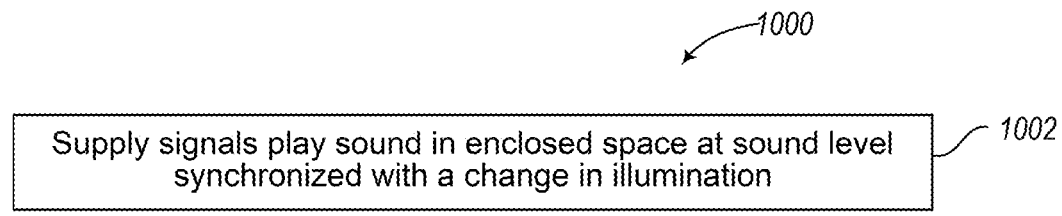
FIG. 10 is a flow diagram that shows a low level method of operating one or more components of a habitable environment enhancement system for adjusting an acoustical aspect of a habitable environment, according to one illustrated embodiment, which may be useful in performing at least a portion of the method illustrated in FIG. 3.

FIG. 10 shows a low level method 1000 of operating one or more components of a habitable environment enhancement system for adjusting an acoustical aspect of a habitable environment, according to one illustrated embodiment, which may be useful in performing at least a portion of the method 300 illustrated in FIG. 3.

The method 1000 may, for example start on a periodic basis, for instance every few minutes, hourly, or daily. Alternatively, or additionally, the method 1000 may start on demand, for instance in response to a request by a guest or operator of a facility (e.g., hotel, spa). Alternatively or additionally, the method 1000 may start in response to a call or signal from a program executed by the control subsystem, for instance in synchronization with some other aspect of the environment. For instance, sound may be triggered by an alarm clock setting, which is synchronized with light levels and/or spectrum.

In particular, the control subsystem provides signals which cause at least one speaker to play sound in the enclosed space at a sound level that changes in synchronization with a change in a level of illumination emitted by the illumination sources at 1004.

The low level method 1000 may terminate until called again, or may continually repeat. Alternatively, the method 1000 may run concurrently with other methods or processes, for example, as one of multiple threads on a multi-threaded processor system.

Modifications

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems, not necessarily the exemplary system generally described above.

The control subsystem or some other processor-based system such as a personal computer, may be programmed to evaluate a "wellness" of a given space. The system may assess various amenities provided in the environmental space, including type and effectiveness of the amenities. For instance, the system may assign points for particular types of amenities and/or effectiveness. For example, points may be assigned for having an active lighting subsystem, which additional points for active lighting can positively influence circadian patterns. Also for example, points may be assigned for air treatment, with a total number of points based on effectiveness of the air treatment. Also for example, points may be assigned for water treatment, with a total number of points based on effectiveness of the water treatment. Points may be required in each possible category (e.g., lighting, air, water, sound, reduced use of VOC leaching materials, use of sound absorbent or damping materials, use of materials that cushion or absorb shocks to protect the occupant). Alternatively, points may be required for a subset of categories. Additionally, or alternatively, a minimum number of points may be required in each of a number of categories, or a minimum cumulative score required to obtain a given rank or wellness rating. Ranks or wellness ratings may be certified and used in advertising. Wellness may be reassessed from time to time.

Wellness may be assessed based on self-reported scores or scores assigned by a reviewer or examiner. The scores may be reported via various user input devices, for instance a keyboard, keypad, touch panel associated with a GUI. The scores may, for instance, be entered via a Webpage user interface, and communicated to the system for evaluation. The system may perform comparisons of a given facility from year to year, or between different facilities. The evaluation may be compared or scored against a defined set of wellness standards in each of a number of categories or pathways.

Wellness scores need not be dependent on self-reports, but may be inferred from environmental sensors and occupant-based biometrics. For example, data gathered passively or actively from devices in the built environment, furniture or other biometric-reading devices, can contribute to a personal wellness score, that can be used to directly or indirectly control elements in the built environment including lighting, sound, HVAC or other categories previously discussed. Relevant biometrics may include any health or wellness-related measurements, including but not limited to heart rate, heart-rate variability, sleep phase, sleep length, or respiration rate, walking steps per day, body weight, or BMI.

The control system may cause a display of a dashboard which provides a concise representation of environmental information to occupants of the habitable environment 100 and/or to personnel of the facility (e.g., hotel) which houses the habitable environment 100 (e.g., room or suite). The dashboard may additionally present tips, suggestions, questionnaires, suggested settings, interventions, activities, health/wellness educational information, etc. The dashboard may be presented via a Website or Webpage and/or may be stored "in the cloud". The dashboard may be accessible via any type of processor-based device including mobile devices (e.g., smart phones, tablet computers) as a Webpage or a dedicated application. Such devices may include transducers that act based on the information and/or to control various environmental aspects of the habitable environment via the control subsystem. For example, the Webpage or application may communicatively integrate the mobile device with the lighting subsystem and/or other environmental systems and controls.

For instance, a habitable environment may include any combination of one or more of the passive or active components. Some components may reside in or be controlled as part of a different subsystem than illustrated.

Also for instance, while various methods and/or algorithms have been described, some or all of those methods and/or algorithms may omit some of the described acts or steps, include additional acts or steps, combine acts or steps, and/or may perform some acts or steps in a different order than described. Some of the method or algorithms may be implemented in software routines. Some of the software routines may be called from other software routines. Software routines may execute sequentially or concurrently, and may employ a multi-threaded approach.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs) or programmable gate arrays or programmable logic circuits (PLCs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms taught herein are capable of being distributed as a program product in a variety of forms, and that an illustrative embodiment applies equally regardless of the particular type of signal bearing media used to actually carry out the distribution. Examples of nontransitory signal bearing media include, but are not limited to, the following: recordable type media such as portable disks and memory, hard disk drives, CD/DVD ROMs, digital tape, computer memory, and other non-transitory computer-readable storage media.

U.S. provisional patent application Ser. No. 61/694,125, filed Aug. 28, 2012 and U.S. patent application Ser. No. 14/012,444, filed Aug. 28, 2013 are incorporated herein by reference in their entirety. The various embodiments described above can be combined to provide further embodiments. Aspects of the embodiments can be modified, if necessary or desirable to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for evaluating wellness of a habitable space, the method comprising the steps of:
   receiving wellness information by at least one processor regarding a plurality of amenities associated with a habitable space;
   assessing the plurality of amenities and assigning a point value to each of the plurality of amenities based, at least in part, on the received wellness information; and
   determining a wellness rating for the habitable space based, at least in part, on a combination of the point values assigned to each of the plurality of amenities.

2. The method of claim 1, further comprising:
receiving data associated with at least one of the plurality of amenities from one or more sensors associated with the pluralities of amenities; and
displaying the wellness rating via an input/output subsystem.

3. The method of claim 1, wherein the wellness rating is obtained for a first time period and the method further comprising:
comparing the wellness rating for the habitable space to a second wellness rating.

4. The method of claim 3, wherein the second wellness rating is obtained for the habitable space for a second time period.

5. The method of claim 3, wherein the second wellness rating is obtained for a second habitable space.

6. The method of claim 3, further comprising:
sending a signal indicative of a comparison between the wellness ranking for the habitable space and the second wellness rating.

7. The method of claim 1, wherein at least one of the plurality of amenities is related to at least one of:
an active lighting subsystem associated with the habitable space;
an air treatment subsystem associated with the habitable space; and
a water treatment subsystem associated with the habitable space.

8. The method of claim 7, wherein a point value associated with at least one of the active lighting subsystem, the air treatment subsystem, or the water treatment subsystem associated with the habitable space is based at least in part on at least one of:
a type of the lighting;
effectiveness of the lighting;
effectiveness of the air treatment subsystem;
a type of the air treatment subsystem;
an ability of the air treatment subsystem to reduce VOCs in the habitable space;
effectiveness of the water treatment subsystem; and
a type of the water treatment subsystem.

9. The method of claim 1, further comprising:
comparing the wellness rating for the habitable space to a defined set of wellness standards.

10. The method of claim 1, further comprising at least one of the following:
displaying information regarding the wellness rating and at least one of the plurality of amenities;
displaying information regarding the wellness rating and the habitable environment;
displaying information regarding the wellness rating and at least one occupant of the habitable environment;
sending a signal indicative of the wellness rating and at least one of the plurality of amenities;
sending a signal indicative of the wellness rating and the habitable environment;
sending a signal indicative of the wellness rating and at least one occupant of the habitable environment;
sending a signal indicative of an intervention associated with the habitable environment; and
sending a signal indicative of a change to an environmental setting for the habitable environment.

11. The method of claim 1, further comprising:
identifying an occupant of the habitable environment, via one or more environment sensors.

12. The method of claim 1, further comprising:
receiving updated wellness information by the at least one processor;
reassessing the wellness rating associated with the habitable environment; and
updating the wellness rating via the at least one processor.

13. The method of claim 1, wherein receiving information regarding a plurality of amenities associated with a habitable space includes at least one of:
receiving information from a sensor located within the habitable space;
receiving information from an input/output subsystem; and
receiving information from a biometric reading device within the habitable space.

14. A system for determining a wellness rating for a habitable space, comprising:
at least one nontransitory processor-readable medium communicatively coupled to at least one processor and which stores at least one of instructions or data executable by the at least one processor and a plurality of active subsystems operable to determine a wellness rating for a habitable space by, at least in part:
receiving wellness information by the at least one processor regarding a plurality of amenities associated with the habitable space;
assessing the plurality of amenities and assigning a point value to each of the plurality of amenities; and
determining a wellness rating for the habitable space based, at least in part, on a combination of the point values assigned to each of the plurality of amenities.

15. A method for evaluating wellness of a habitable space, comprising the steps of:
identifying a plurality of amenities associated with a habitable space;
assigning a point value to each of the plurality of amenities, wherein a point value associated with a particular amenity is assigned based on at least one of a type and an effectiveness of the particular amenity; and
determining a wellness rating for the habitable space based, at least in part, on a combination of the point values assigned to each of the plurality of amenities.

16. A method for evaluating wellness of a habitable space, comprising the steps of:
determining a plurality of wellness categories for a habitable space;
determining a point value for each of the plurality of wellness categories; and
determining a wellness rating for the habitable space based, at least in part, on the point values for the plurality of wellness categories.

17. The method of claim 16, further comprising at least one of the following:
determining a minimum wellness rating;
determining a minimum point value for each of the plurality of wellness categories; and
determining if each point value meets a minimum requirement.

18. The method of claim 16, wherein determining a wellness rating for the habitable space based, at least in part, on the point values for the plurality of wellness categories, only occurs if each point value meets a minimum requirement.

19. The method of claim 16, further comprising at least one of:

identifying at least one amenity in the habitable space for each of the plurality of wellness categories; and identifying an individual associated with the habitable space.

20. The method of claim 19, further comprising at least one of:

sending wellness rating information to an electronic user device of the individual associated with the habitable space;

sending amenity point value information to an electronic user device of the individual associated with the habitable space;

sending amenity point value information to a device associated with the habitable space; and sending data indicative of the point values for the plurality of wellness categories to a device associated with the habitable space.

21. A method for establishing a wellness rating for a habitable space, comprising the steps of:

determining a point value for each of a plurality of wellness categories associated with a habitable space and a wellness ranking for the habitable space; and determining the wellness rating for the habitable space based, at least in part, on the point values for the plurality of wellness categories for the habitable space.

22. A method for evaluating wellness of a habitable space, comprising the steps of:

identifying a plurality of wellness categories associated with a wellness ranking;

identifying at least one amenity for a habitable space for each of the plurality of wellness categories;

determining a score for each identified amenity; and determining the wellness ranking for the habitable space based, at least in part, on the scores for the identified amenities.

23. The method of claim 22, wherein a score for an amenity is based, at least in part, on at least one of:

an effectiveness of the amenity;

an availability of the amenity in the habitable space; and data generated by a sensor in the habitable space and associated with the amenity.

24. The method of claim 22, wherein a minimum score is required for an identified amenity before the wellness ranking is determined.

25. The method of claim 22, wherein a minimum total score is required before the wellness ranking is determined.

26. A method for evaluating wellness of a habitable space, comprising the steps of:

receiving wellness information regarding a plurality of amenities associated with a habitable space, wherein the plurality of amenities relate to at least two of the following, lighting within the habitable space, air quality within the habitable space, use of VOC leaching materials within the habitable space, use of sound dampening materials within the habitable space, and water quality within the habitable space;

assigning a point value to each of the plurality of amenities;

determining a wellness rating for the habitable space based, at least in part, on a combination of the point values assigned to each of the plurality of amenities; and sending data indicative of the wellness rating.

\* \* \* \* \*